US006794128B2

(12) United States Patent
Marks et al.

(10) Patent No.: US 6,794,128 B2
(45) Date of Patent: Sep. 21, 2004

(54) METHODS OF SELECTING INTERNALIZING ANTIBODIES

(75) Inventors: James D. Marks, Kensington, CA (US); Marie Alix Poul, San Francisco, CA (US); Baltazar Becerril, Morelos (MX)

(73) Assignee: The Regents of the University of California, Oakland, CA (US)

( * ) Notice: Subject to any disclaimer, the term of this patent is extended or adjusted under 35 U.S.C. 154(b) by 31 days.

(21) Appl. No.: 09/249,529

(22) Filed: Feb. 12, 1999

(65) Prior Publication Data

US 2001/0008759 A1 Jul. 19, 2001

Related U.S. Application Data

(60) Provisional application No. 60/082,953, filed on Apr. 24, 1998.

(51) Int. Cl.[7] ........................... C12Q 1/00; G01N 33/53; C12N 15/00
(52) U.S. Cl. .................... 435/5; 435/4; 435/6; 435/7.1; 435/7.2; 435/320.1; 435/DIG. 1; 435/DIG. 2; 435/DIG. 3; 435/DIG. 4; 435/DIG. 14; 435/DIG. 15; 436/501; 436/518; 536/23.1; 536/23.53
(58) Field of Search .......................... 435/4, 5, 6, 7.1, 435/7.2, 320.1, DIG. 1, DIG. 2, DIG. 3, DIG. 4, DIG. 14, DIG. 15; 436/501, 518, 512; 536/23.1, 23.53; 530/387.1, 387.9, 388.1

(56) References Cited

U.S. PATENT DOCUMENTS

| | | |
|---|---|---|
| 5,696,237 A | 12/1997 | Fitzgerald et al. |
| 5,733,782 A | 3/1998 | Dorai et al. |
| 5,885,793 A | 3/1999 | Griffeths et al. |
| 6,054,312 A * | 4/2000 | Larocca et al. .............. 435/7.1 |

OTHER PUBLICATIONS

Ewjik et al., Proc. Natl. Acad. Sci. USA, vol. 94, pp. 3903–3908, Apr. 1997.*
Strausbol–Gron et al., FEBS Letters, vol. 39, pp. 71–75, 1996.*
Adams et al., "Prolonged in vivo tumour retention of a human diabody targeting the extracellular domain of human HER2/neu", British Journal of Cancer, May 1998, vol. 77, No. 9, pp. 1405–1412.
Adams et al., "Increased Affinity Leads to Improved Selective Tumor Delivery of Single–Chain Fv Antibodies", Cancer Research, Feb. 1998, vol. 58, No. 3, pp. 485–490.
Altenschmidt et al., "Targeted Therapy of Schwannoma Cells in Immunocompetent Rats with an erbB2–Specific Antibody–Toxin", International Journal of Cancer, Sep. 26, 1997, vol. 73, No. 1, pp. 117–124.
Hudziak et al., p185her2 Monoclonal Antibody has Antiproliferative Effects in Vitro and Sensitizes Human Breast Tumor Cells to Tumor Necrosis Factor, Molecular and Cellular biiology, Mar. 1989, vol. 9, No. 3, pp. 1165–1172.

(List continued on next page.)

*Primary Examiner*—Padmashri Ponnaluri
(74) *Attorney, Agent, or Firm*—Angela P. Horne; Tom Hunter; Quine Intellectual Property Law Group, P.C.

(57) ABSTRACT

This invention provides methods of selecting antibodies that are internalized into target cells. The methods generally involve contacting target cells with one or more members of an antibody phage display library. The members of the phage display library are also contacted with cells of a subtractive cell line. The target cells are then washed to remove the subtractive cell line cells and members of the phage display library that are non-specifically bound or weakly bound to the target cells. The target cells are cultured under conditions where members of the phage display library can be internalized if bound to an internalizing marker and internalized members of the phage display library are then identified.

42 Claims, 7 Drawing Sheets

OTHER PUBLICATIONS

Hurwitz et al., "Suppression and promotion of tumor growth by monoclonal antibodies to ErbB–2 differentially correlate with cellular uptake", Proceedings of the National Academy of Sciences, Apr. 11, 1995, vol. 92, No. 8, 3353–3357.

Kirpotin et al., "Sterically Stabilized Anti–HER2 Immunoliposomes: Design and Targeting to Human Breast Cancer Cells in Vitro", Biochemistry, Jan. 7, 1997, vol. 36, No. 1, pp. 66–75.

Lewis et al., Differential responses of human tumor cell lines to anti–p185her2 monoclonal antibodies, Cancer, Immunology, Immunotherapy, Mar. 1993, vol. 37, No. 4, pp. 255–263.

Pereira et al., A model system for detection and isolation of a tumor cell surface antigen using antibody phage display, Journal of Immunological Methods, Apr. 11, 1997, vol. 203, No. 1, pp. 11–24.

Sheets et al., "Efficient construction of a large nonimmune phage antibody library: The production of high–affinity human single–chain antibodies to protein antigens", Proceedings of the National Academy of Sciences, May 26, 1998, vol. 95, No. 11, 6157–6162.

Slamon, et al., Studies of the HER–2/neu Proto–oncogene in Human Breast and Ovarian Cancer, American Association for the Advancement of Science, May 12, 1989, vol. 244, No. 4905, pp. 707–712.

Stancovski, et al., "Mechanistic aspects of the opposing effects of monoclonal antibodies to the ERBB2 receptor on tumor growth", Proceedings of the National Academy of Sciences, Oct. 1, 1991, vol. 88, No. 19, pp. 8691–8698.

Ullrich, et al., "Signal Transduction by Receptors with Tyrosine Kinase Activity", Cell, Apr. 20, 1990, vol. 61, No. 2, pp. 203–212.

Yarden, Yosef, "Agonistic antibodies stimulate the kinase encoded by the neu protooncogene in living cells but the oncogenic mutant is constitutively active", Proceedings of the National Academy of Sciences, Apr. 1990, vol. 87, No. 7, pp. 2569–2573.

Watters, et al., "An optimized method for cell–based phage display panning", Immunotechnology, 1997, vol. 3, pp. 21–29.

Barry, et al., "Toward cell–targeting gene therapy vectors: Selection of cell–binding peptides from random peptide–presenting phage libraries", Nature Medicine, Mar. 1996, vol. 2, No. 3, pp. 299–305.

Fominaya, et al., "Target Cell–specific DNA Transfer Mediated by a Chimeric Multidomain Protein", Journal of Biological Chemistry, May 3, 1996, vol. 271, No. 18, pp. 10560–10568.

Hart, et al., "Cell Binding and Internalization by Filamentous Phage Displaying a Cyclic Arg–Gly–Asp–containing Peptide", Journal of Biological Chemistry, Apr. 29, 1994, vol. 269, No. 17, pp. 12468–12474.

Larocca et al., "Targeting Bacteriophage to Mammalian Cell Surface Receptor for Gene Delivery", Human Gene Therapy, Nov. 1, 1998, vol. 9, pp. 2393–2399.

Marks, et al, "Molecular Evolution of Proteins on Filamentous Phage", Journal of Biological Chemistry, Aug. 15, 1992, vol. 267, No. 23, pp. 16007–16010.

Okayama, et al., "Bacteriophage Lambda Vector for Transducing a cDNA Clone Library into Mammalian Cells", Molecular and Cellular Biology, May 1985, vol. 5, No. 5, pp. 1136–1142.

Schier, et al., "Identification of functional and structural amino–acid residues by parsimonious mutagenesis", Gene, Mar. 9, 1996, vol. 169, No. 2, pp. 147–155.

Schier, et al., "Efficient in vitro affinity maturation of phage antibodies using BIAcore guided selections", Hum. Antibod. Hybridomas, 1996, vol. 3, No. 7, pp. 97–105.

Schier, et al., "In vitro and in vivo characterization of a human anti–c–erbB–2 single–chain Fv isolated from a filamentous phage antibody library", Immunotechnology, 1995, vol. 1, pp. 73–81.

Schier, et al., "Isolation of High–affinity Monomeric Human Anti–c–erB–2 Single chain Fv Using Affinity–driven Selection", Journal of Molecular Biology, Jan. 12, 1996, vol. 255, No. 1, pp. 28–43.

Schier, et al., "Isolation of Picomolar Affinity Anti–c–erbB–2 Single–chain Fv by Molecular Evolution of the Complementarity Determining Regions in the Center of the Antibody Binding Site", Journal of Molecular Biology, Jan. 12, 1996, vol. 263, No. 4, pp. 551–567.

Vaughan, et al., "Human Antibodies with sub–nanomolar Affinities Isolated from a Large Non–immunized Phage Display Library", Nature Biotechnology, Mar. 1996, vol. 14, pp. 309–314.

Yokoyama–Kobayashi, et al., "Recombinant fl Phage Particles Can Transfect Monkey COS–7 Cells by DEAE Dextran Method", Biochemical and Biophysical Research Communication, Apr. 30, 1993, vol. 192, No. 2, pp. 935–939.

Larocca et al. (1999) "Gene Transfer to Mammalian Cells Using Genetically Targeted Filamentous Bacteriophage," *FASEB Journal*, 13(6):727–734.

* cited by examiner

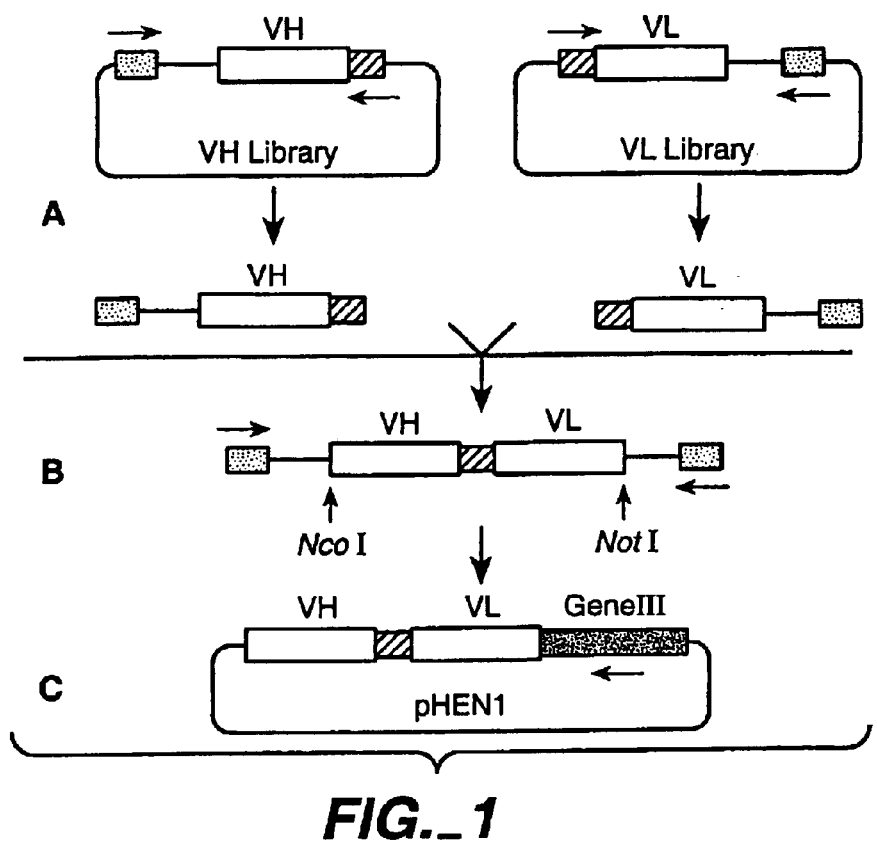
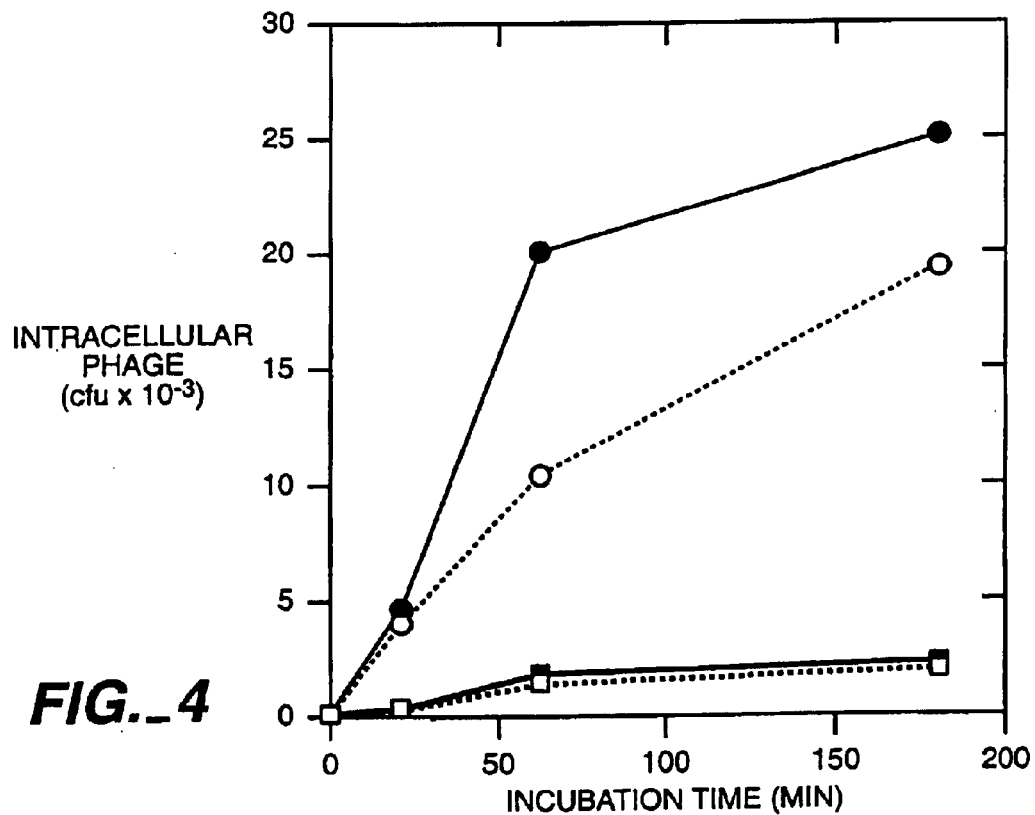

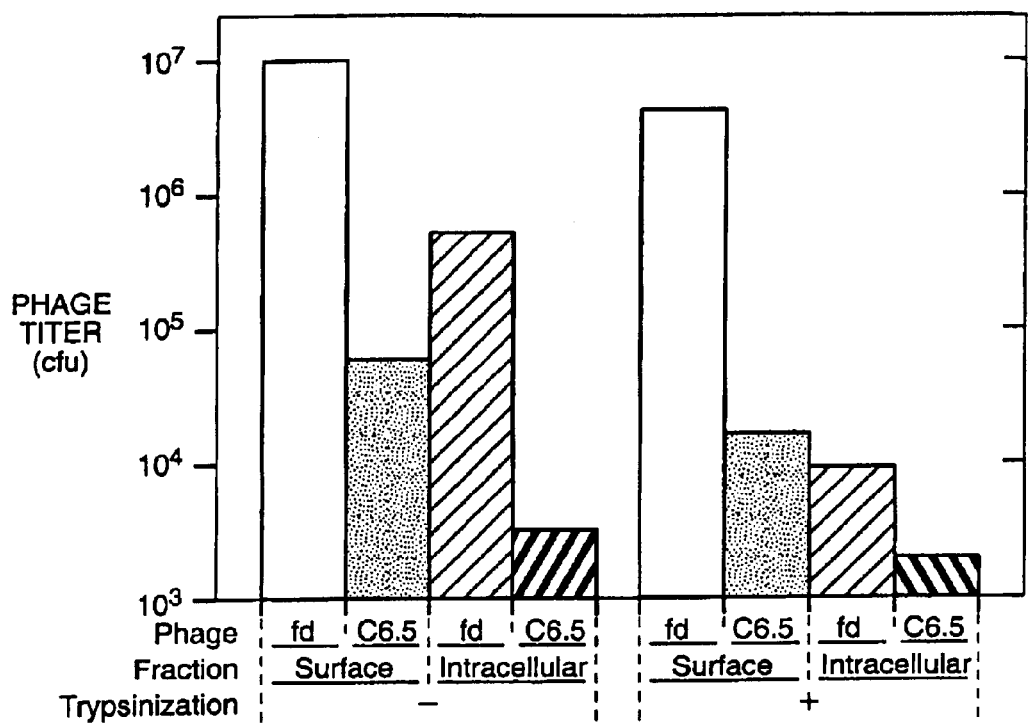
FIG._3
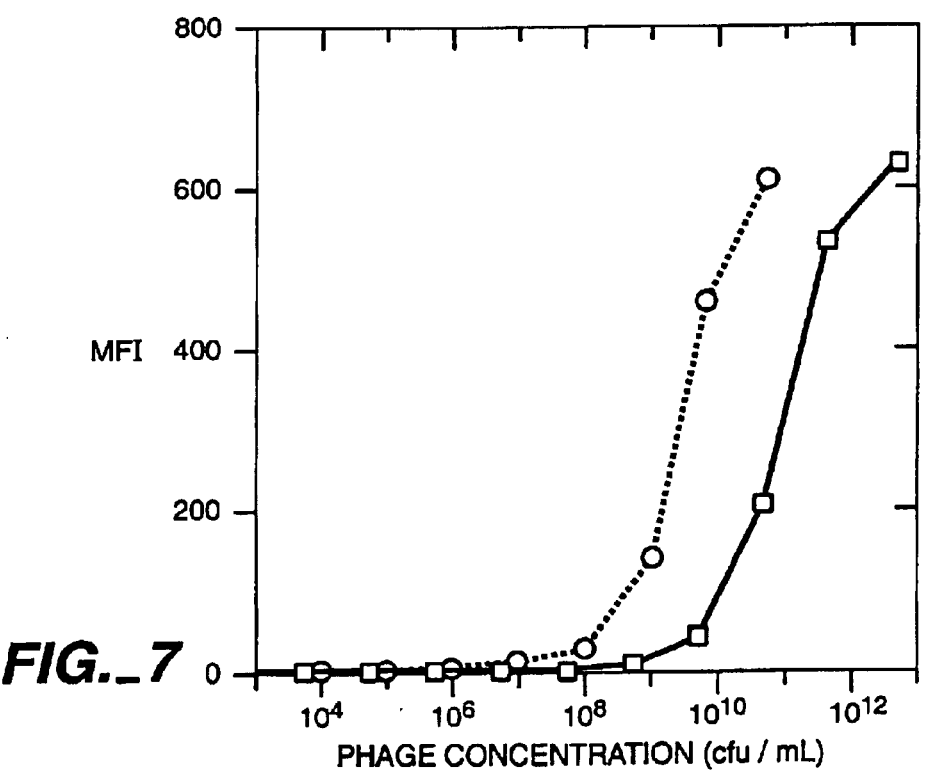
FIG._7

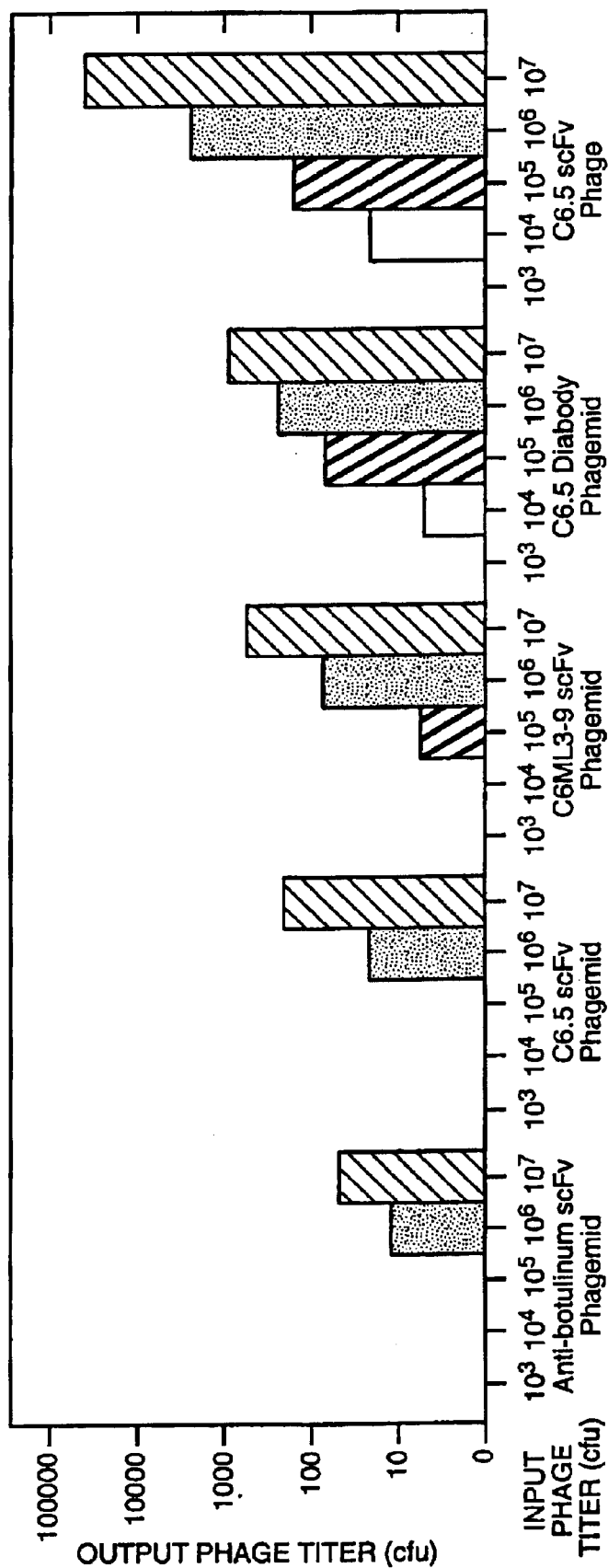
FIG._5

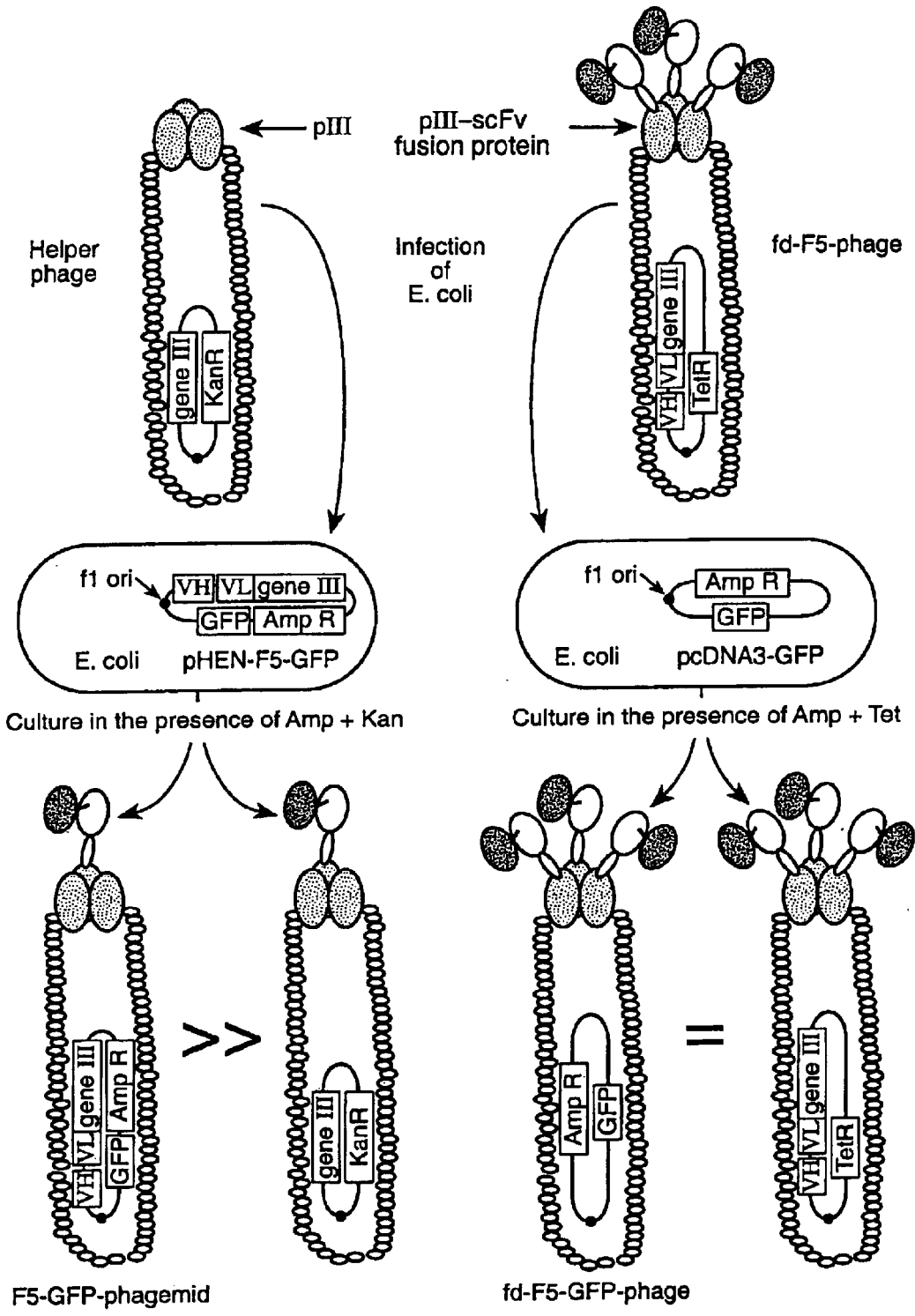
FIG._6

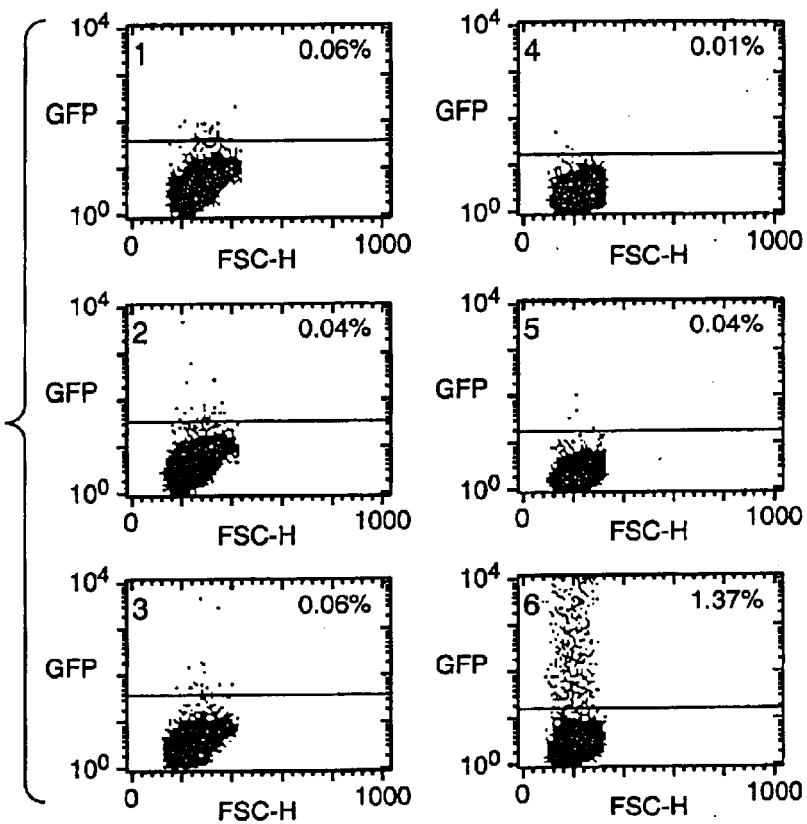
FIG._8A
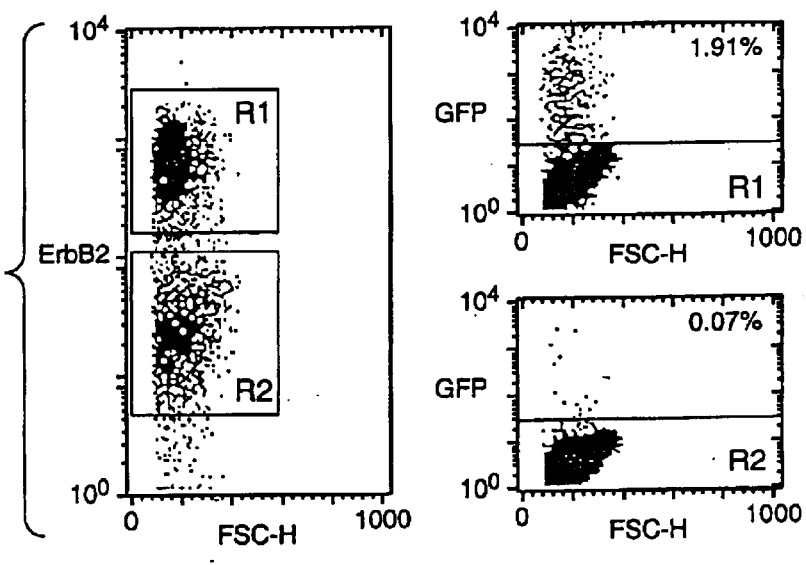
FIG._8B

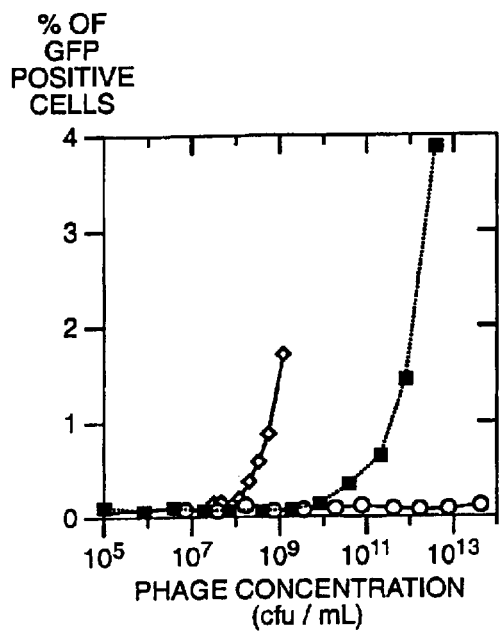
FIG._9A
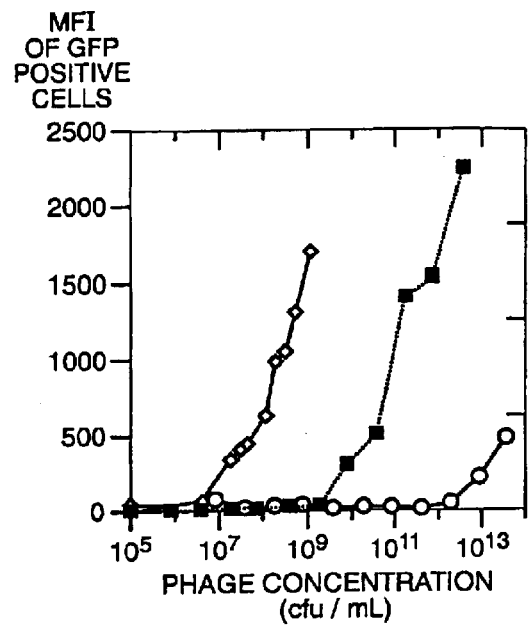
FIG._9B
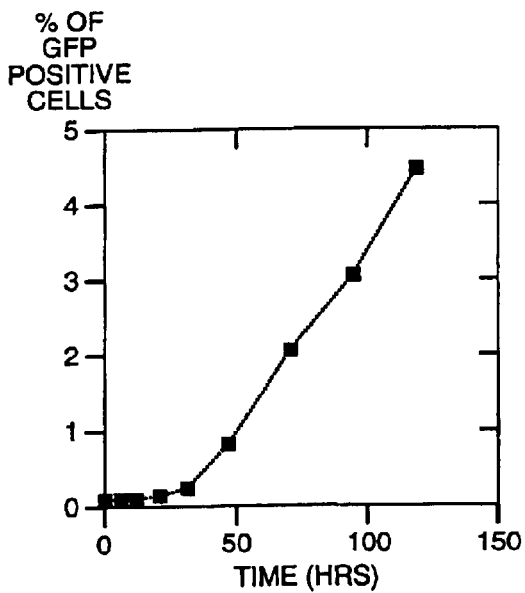
FIG._9C
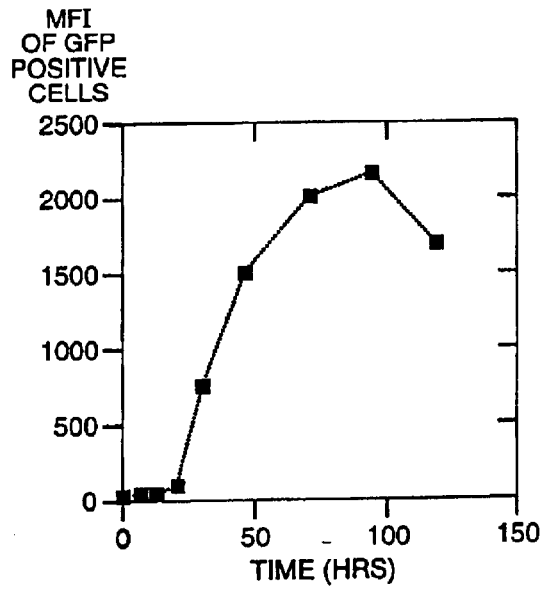
FIG._9D

METHODS OF SELECTING INTERNALIZING ANTIBODIES

CROSS-REFERENCE TO RELATED APPLICATIONS

This application claims benefit under 35 U.S.C. §19(e) of provisional application USSN 60/082,953, filed on Apr. 24, 1998, which is herein incorporated by reference in its entirety for all purposes.

STATEMENT AS TO RIGHTS TO INVENTIONS MADE UNDER FEDERALLY SPONSORED RESEARCH AND DEVELOPMENT

This work was supported, in part, by Department of Defense Grants DAMD17-96-1-6244 and DAMD17-94-4433. The government of the United States of America may have some rights in this invention.

FIELD OF THE INVENTION

This invention pertains to the fields of immunodiagnostics and immunotherapeutics. The invention provides methods of identifying internalizing antibodies and internalizing receptor ligands, as well as the internalizing receptors bound.

BACKGROUND OF THE INVENTION

Growth factor receptors, and other signal transduction receptors, are frequently overexpressed in human carcinomas and other diseases and thus have been utilized for the development of targeted therapeutics. The HER2/neu gene, for example, is amplified in several types of human adenocarcinomas, especially in tumors of the breast and the ovary (Slamon et al. (1989) *Science* 244: 707–712) leading to the overexpression of the corresponding growth factor receptor ErbB2. Targeting of ErbB2 overexpressing cells has been accomplished primarily using anti-ErbB2 antibodies in different formats, including conjugation to liposomes containing chemotherapeutics (Kirpotin et al. (1997). *Biochem.* 36: 66–75), fusion to DNA carrier proteins delivering a toxic gene (Forminaya and Wels (1996) *J. Biol Chem.* 271: 10560–10568), and direct fusion to a toxin (Altenschmidt et al. (1997) *Int. J Cancer* 73: 117–124).

For many of these targeted approaches, it is necessary to deliver the effector molecule across the cell membrane and into the cytosol. In some cases, this can be facilitated by taking advantage of receptor mediated endocytosis (Ullrich and Schlessinger (1990) *Cell* 61: 203–212). Receptor-mediated endocytosis is often caused when ligand binding causes receptor activation via homo- or heterodimerization, either directly for bivalent ligand or by causing a conformational change in the receptor for monovalent ligand. Antibodies can mimic this process, stimulate endocytosis, become internalized and deliver their payload into the cytosol. In addition, the efficiency with which antibodies mediate internalization differs significantly depending on the type of the antibody (e.g. whole antibody, fragment, single chain, monomeric, dimeric, etc.) and on the epitope recognized (Yarden (1990) *Proc. Natl. Acad. Sci. USA* 87: 2569–2573; Hurwitz et al (1995) *Proc. Natl. Acad. Sci. USA* 92: 3353–3357.). Thus for some applications, such as liposomal targeting, only antibodies that bind specific epitopes are rapidly internalized and yield a functional targeting vehicle.

Internalizing antibodies have also been shown to cause cell growth inhibition or enhanced cell growth, depending on the epitope recognized. Thus selection for internalization should lead to the isolation of growth inhibitory or stimulatory (agonist) antibodies. Such inhibitory antibodies might be used as cancer treatments or for the treatment of other conditions characterized by cell hyperproliferation, and for the treatment of inflammation (anti-inflammatories). Agonist antibodies could be used for stimulating growth of relevant cells (for example stem cells). Targeting of cells besides cancer cells for gene delivery will also have many application Currently, antibodies that mediate internalization are identified by screening hybridomas. Screening of hybridoma-produced antibodies, however, is laborious, time-consuming, and expensive.

SUMMARY OF THE INVENTION

This invention is based, in part, on the discovery that it is possible to directly select internalizing antibodies from large non-immune phage libraries by recovering infectious phage particles from within cells after receptor mediated endocytosis.

Thus, in one embodiment, this invention provides methods of selecting polypeptide or antibody binding moieties that are internalized into target cells. The methods preferably involve i) contacting one or more of target cells with one or more members of a phage display library; iv) culturing the target cells under conditions where members of the display library can be internalized if bound to an internalizing marker; and v) identifying internalized members of the phage display library if members of the phage display library are internalized into one or more of the target cells. The methods also optionally, and preferably additionally involve contacting members of the phage display library with a cells of a subtractive cell line; and then washing the target cells to remove the cells of a subtractive cell line and to remove members of the phage display library that are non-specifically bound or weakly bound to the target cells. In a preferred embodiment, the phage display library is an antibody phage display library, more preferably an antibody phage display library displaying single chain antibodies (e.g. scFv, scFab, etc.).

In a preferred embodiment, the "identifying" step comprises recovering internalized phage and repeating steps the process again to further select for internalizing binding moieties. In one embodiment, the "recovering" step involves lysing the target cells to release internalized phage; and infecting a bacterial host with the internalized phage to produce phage for a subsequent round of selection. The recovering step can involve recovering infective phage, and/or recovering a nucleic acid encoding a phage-displayed antibody and/or selection of phage expressing a selectable marker (e.g. an antibiotic resistance gene or cDNA). The identifying step can involve detecting expression of a reporter gene, detecting the presence absence or quantity of a particular nucleic acid, or selection of phage via a selectable marker. In preferred methods the cells of a subtractive cell line are present in at least 2-fold excess over the target cells. In preferred methods, the target cells form an adherent layer. In preferred methods the target cell line is grown adherent to a tissue culture plate and co-incubated with the subtracting cell line in suspension in a single cell culture flask. In particular preferred methods, the contacting with a subtractive cell line is performed at a temperature (e.g. at about 4° C.) lower than the internalization culture conditions (e.g. at about 37°)

In particularly preferred embodiments, the phage express a selectable maker and/or a reporter gene. Preferred selectable markers include, but are not limited to genes (or cDNAs) encoding fluorescent protein(s), an antibiotic resistance gene or cDNA, and a chromagenic gene or cDNA (e.g., horse radish peroxidase, β-lactamase, luciferase, and β-galactosidase. In certain embodiments the target cells can include solid tumor cells, members of a cDNA expression library, cells that overexpress a cytokine receptor, cells that overexpress a growth factor receptor, metastatic cells, cells of a transformed cell line, cells transformed with a gene or cDNA encoding a specific surface target receptor, and neoplastic cells derived from outside a solid tumor. In one particularly preferred embodiment, the said cells of a subtractive cell line are selected from the same tissue type as the target cells. Suitable s subtractive cell line cells include, but are not limited to fibroblasts, monocytes, stem cells, and lymphocytes.

The methods of this invention can also be used to identify internalizing receptors and/or internalizing receptor epitopes (regions of the receptor that when bound induce internalization of the binding moiety). The methods generally involve any of the methods for identifying internalizing antibodies or polypeptides as described herein with the additional steps whereby the internalizing antibodies or polypeptides identified are used to probe the original target cells, or different cells. When the internalizing antibodies or polypeptides so bind, they permit isolation of the cell bearing the internalizing receptor and isolation of the receptor and/or receptor epitope itself. Thus in one embodiment the methods involve i) contacting one or more of the target cells with one or more members of a phage display library; ii) optionally, but preferably, contacting members of the phage display library with a cells of a subtractive cell line; iii) optionally, but preferably washing the target cells to remove said cells of a subtractive cell line and to remove members of the phage display library that are non-specifically bound or weakly bound to said target cells; iv) culturing the cells under conditions where members of said phage display library can be internalized if bound to an internalizing marker; v) identifying internalized members of the phage display library if members of the phage display library are internalized into one or more of said target cells; vi) contacting the same or different target cells with the identified internalized members of step (v) or members propagated therefrom, whereby the members bind to the surface of said same or different target cells. The method can further involve isolating a component of the same or different target cells to which the members bind. In some methods the "identifying" step involves recovering internalized phage and repeating steps (i) through (v) to further select for internalizing binding moieties.

The contacting, washing, culturing, and identifying steps are preferably performed as described herein and the target and subtractive cells include the cells described herein.

In still another embodiment, this invention provides a multivalent antibody phage display library. The library preferably comprises a plurality of phage wherein the phage display, on average, at least two copies of a single-chain antibody and the library comprises a plurality of species of single-chain antibody. In preferred embodiments, the phage display, on average, at least 3, at least 4, or at least 5 copies of a single chain antibody per phage particle. Particularly preferred libraries comprise, on average, at least $10^5$, preferably at least $10^6$, more preferably at least $10^7$, and most preferably at least $10^8$ different species of single chain antibody. In a most preferred embodiment, the antibodies are encoded by a nucleic acids that are phage (not phagemid) vectors.

In certain embodiments, the library will be selected for members that specifically bind to an internalizing cell surface receptor (e.g. erbB2, EGF receptor, PDGF receptor, VEGF receptor, transferrin receptor, etc.). The single-chain antibodies are preferably single chain Fv (scFv) or single-chain Fab (scFab) antibodies. Filamentous phage are preferably used in the libraries of this invention and the antibodies are preferably expressed as a fusion with a PIII minor coat protein. The phage can also express a selectable marker (e.g. an antibiotic resistance gene or cDNA) and/or a reporter gene or cDNA (e.g., green fluorescent protein (GFP), Fflux, β-gal, β-lactamase, etc.).

In still yet another embodiment, this invention provides a nucleic acid library encoding one of the phage display antibody libraries describe herein. The nucleic acid library comprises at least $10^5$, more preferably at least $10^6$, and most preferably at least $10^7$ different phage or phagemid vectors.

This invention also provides kits for practice of the methods described herein. The kits preferably comprise one or more containers containing a phage display library (or a portion thereof) described herein. The kit can include nucleic acids encoding the library and/or phage particles expressing single chain antibodies (preferably a multivalent library) and/or cells containing the intact phage or nucleic acids from the phage.

DEFINITIONS

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (scFv or scFv) in which a variable heavy and a variable light chain are joined together (directly or through a peptide linker) to form a continuous polypeptide. The single chain Fv antibody is a covalently linked $V_H$–$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879–5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No: 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies include all those that have been displayed on phage I think preferred antibodies should include all that have been displayed on phage (e.g., scFv, Fv, Fab and disulfide linked Fv (Reiter et al. (1995) *Protein Eng.* 8: 1323–1331).

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_d$) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity and is thus equal to the dissociation constant $K_d$ (see, generally, Davies et al. (1990) *Ann. Rev. Biochem.*, 59: 439–473.

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, F5 or C1 antibodies can be raised to the c-erbB-2 protein that bind c-erbB-2 and not to other proteins present in a tissue sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The terms "polypeptide", "peptide", or "protein" are used interchangeably herein to designate a linear series of amino acid residues connected one to the other by peptide bonds between the alpha-amino and carboxy groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids, which include, but are not limited to those listed in 37 CFR ]1.822(b)(4). Furthermore, it should be noted that a dash at the beginning or end of an amino acid residue sequence indicates either a peptide bond to a further sequence of one or more amino acid residues or a covalent bond to a carboxyl or hydroxyl end group.

The term "binding polypeptide" refers to a polypeptide that specifically binds to a target molecule (e.g. a cell receptor) in a manner analogous to the binding of an antibody to an antigen. Binding polypeptides are distinguished from antibodies in that binding polypeptides are not ultimately derived from immunoglobulin genes or fragments of immunoglobulin genes.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated.

Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19: 5081; Ohtsuka et al. (1985) *J. Biol. Chem.* 260: 2605–2608; and Cassol et al. (1992); Rossolini et al., (1994) *Mol. Cell. Probes* 8: 91–98). The term nucleic acid is used interchangeably with gene, cDNA, and mRNA encoded by a gene.

The terms "isolated" or "biologically pure" refer to material which is substantially or essentially free from components which normally accompany it as found in its native state. However, the term "isolated" is not intended refer to the components present in an electrophoretic gel or other separation medium. An isolated component is free from such separation media and in a form ready for use in another application or already in use in the new application/milieu.

A chimeric molecule is a molecule in which two or more molecules that exist separately in their native state are joined together to form a single molecule having the desired functionality of all of its constituent molecules. While the chimeric molecule may be prepared by covalently linking two molecules each synthesized separately, one of skill in the art will appreciate that where the chimeric molecule is a fusion protein, the chimera may be prepared de novo as a single "joined" molecule.

A fusion protein is a chimeric molecule in which the constituent molecules are all polypeptides and are attached (fused) to each other through terminal peptide bonds so that the chimeric molecule is a continuous single-chain polypeptide. The various constituents can be directly attached to each other or can be coupled through one or more peptide linkers.

An effector moiety or molecule is a molecule or moiety that typically has a characteristic activity that is desired to be delivered to a target cell (e.g. a tumor overexpressing c-erbB-2). Effector molecules include cytotoxins, labels, radionuclides, ligands, antibodies, drugs, liposomes, and viral coat proteins that render the virus capable of infecting a c-erbB-2 expressing cell.

A "target" cell refers to a cell or cell-type that is to be specifically bound by a member of a phage display library or a chimeric molecule of this invention. Preferred target cells are cells for which an internalizing antibody or binding polypeptide is sought. The target cell is typically characterized by the expression or overexpression of a target molecule that is characteristic of the cell type. Thus, for example, a target cell can be a cell, such as a tumor cell, that overexpresses a marker such as c-erbB-2.

A "targeting moiety" refers to a moiety (e.g. a molecule) that specifically binds to the target molecule. Where the target molecule is a molecule on the surface of a cell and the targeting moiety is a component of a chimeric molecule, the targeting moiety specifically binds the chimeric molecule to the cell bearing the target. Where the targeting moiety is a polypeptide it can be referred to as a "targeting polypeptide".

The terms "internalizing" or "internalized" when used in reference to a cell refer to the transport of a moiety (e.g. phage) from outside to inside a cell. The internalized moiety can be located in an intracellular compartment, e.g. a vacuole, a lysosome, the endoplasmic reticulum, the golgi apparatus, or in the cytosol of the cell itself.

An internalizing receptor or marker is a molecule present on the external cell surface that when specifically bound by an antibody or binding protein results in the internalization of that antibody or binding protein into the cell. Internalizing receptors or markers include receptors (e.g., hormone, cytokine or growth factor receptors) ligands and other cell surface markers binding to which results in internalization.

The term "heterologous nucleic acid" refers to a nucleic acid that is not native to the cell in which it is found or whose ultimate origin is not the cell or cell line in which the "heterologous nucleic acid" is currently found.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen. Anti-idiotypic antibodies can also be generated by immunization with an antibody, or fragment thereof., A "phage display library" refers to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

An "antibody library" refers to phage display library that displays antibodies (binding proteins encoded by one or more antibody genes or cDNAs). The antibody library includes the population of phage or a collection of vectors encoding such a population of phage, or cell(s) harboring such a collection of phage or vectors. The library can be monovalent, displaying on average one single-chain antibody per phage particle or multi-valent displaying, on average, two or more single chain antibodies per viral particle. Preferred antibody libraries comprise on average more than $10^6$, preferably more than $10^7$, more preferably more than $10^8$, and most preferably more than $10^9$ different members (i.e. encoding that many different antibodies).

The term "filamentous phage" refers to a viral particle capable of displaying a heterogenous polypeptide on its surface. Although one skilled in the art will appreciate that a variety of bacteriophage may be employed in the present invention, in preferred embodiments the vector is, or is derived from, a filamentous bacteriophage, such as, for example, f1, fd, Pf1, M13, etc. The filamentous phage may contain a selectable marker such as tetracycline (e.g., "fd-tet"). Various filamentous phage display systems are well known to those of skill in the art (see, e.g., , Zacher et al. (1980) *Gene* 9: 127–140, Smith et al.(1985) *Science* 228: 1315–1317 (1985); and Parmley and Smith (1988) *Gene* 73: 305–318).

A "viral packaging signal" is a nucleic acid sequence necessary and sufficient to direct incorporation of a nucleic acid into a viral capsid.

An assembly cell is a cell in which a nucleic acid can be packaged into a viral coat protein (capsid). Assembly cells may be infected with one or more different virus particles (e.g. a normal or debilitated phage and a helper phage) that individually or in combination direct packaging of a nucleic acid into a viral capsid.

The term "detectable label" refers to any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. DynabeadsTM), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., LacZ, CAT, horse radish peroxidase, alkaline phosphatase and others, commonly used as detectable enzymes, either as marker gene products or in an ELISA), and calorimetric labels such as colloidal gold or colored glass or plastic (e.g. polystyrene, polypropylene, latex, etc.) beads. Those detectable labels that can be expressed by nucleic acids are referred to as "reporter genes" or "reporter gene products".

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) Science, 281: 2013–2016). Similarly, highly fluorescent quantum dots (zinc sulfide-capped cadmium selenide) have been covalently coupled to biomolecules for use in ultra-sensitive biological detection (Warren and Nie (1998) Science, 281: 2016–2018).

The following abbreviations are used herein: AMP, ampicillin; c-erbB-2 ECD, extracellular do in of c-erbB-2; CDR, complementarity determining region; ELISA, enzyme linked immunosorbent a say; FACS, fluorescence activated cell sorter; FR, framework region; Glu, glucose; HBS, hepes buff red saline, 10 mM hepes, 150 mM NaCl, pH 7.4; IMAC, immobilized metal affinity chromatography; $k_{on}$, association rate constant; $k_{off}$, dissociation rate constant; MPBS, skimmed milk powder in PBS; PBS, skimmed milk powder in TPBS; PBS, phosphate buffered saline, 25 mM $NaH_2PO_4$, 125 NaCl, pH 7.0; PCR, polymerase chain reaction; RU, resonance units; scFv or scFv, single-chain Fv fragment; TPBS, 0.05% v/v TWEEN® 20 in PBS; SPR, surface plasmon resonance; $V_k$, immunoglobulin kappa light chain variable region; $V_\lambda$, immunoglobulin lambda light chain variable region; $V_l$, immunoglobulin light chain variable region; $V_H$, immunoglobulin heavy chain variable region; wt, wild type.

BRIEF DESCRIPTION OF THE DRAWINGS

FIG. 1 illustrates the method for construction of a large human scFv phage antibody library. The strategy for library construction involved optimizing the individual steps of library construction to increase both the efficiency of scFv gene assembly and to increase the efficiency of cloning assembled scFv genes. (A). First, mRNA from lymphocytes was used to generate $V_H$ and $V_L$ gene repertoires by RTPCR which were cloned into different vectors to create $V_H$ and $V_L$ gene libraries of $8.0 \times 10^8$ and $7.2 \times 10^6$ members respectively. The cloned V-gene libraries provided a stable and limitless source of $V_H$ and $V_L$ genes for scFv assembly. DNA encoding the peptide $(G_4S)_3$ was incorporated into the 5' end of the $V_L$ library. This permitted generation of scFv genes by PCR splicing 2 DNA fragments. Previously, scFv gene repertoires were assembled from 3 separate DNA fragments consisting of $V_H$, $V_L$, and linker DNA. (B) $V_H$ and $V_L$ gene repertoires were amplified from the separate libraries and assembled into an scFv gene repertoire using overlap extension PCR. The primers used to reamplify the $V_H$ and $V_L$ gene repertoires annealed 200 bp upstream of the 5' end of the $V_H$ genes and 200 bp down stream of the $V_L$ genes. These long overhangs ensured efficient restriction enzyme digestion.(C.) The scFv gene repertoire was digested with NcoI and NotI and cloned into the plasmid pHEN1 as fusions with the M13 gene III coat protein gene ( ) for phage-display.

FIG. 3 shows the effect of trypsinization on the enrichment of antigen specific phage. A mixture of fd phage ($5.0 \times 10^{11}$ cfu) and C6.5 scFv phagemid ($5.0 \times 10^8$ fu) was incubated with SKBR3 cells for 2 hours at 37° C. Washes were performed either as described in Table 6 (−) or cells were trypsinized prior to cell lysis (+). Phage present in the first stripping buffer wash (cell surface phage) and the cell lysate (intracellular phage) were titered in the presence of ampicillin (C6.5 phagemid) or tetracycline (fd phage).

FIG. 4 shows the effect of incubation time and chloroquine on the recovery of antigen specific phage. SKBR3 cells were incubated in the presence (■, ●) or absence (□, ○) of chloroquine (50 µM) for 2 hours prior to the addition of anti-botulinum phagemid (□, ■) or C6.5 scFv phagemid (○, ●) ($1.5 \times 10^9$ cfu/ml). Cell samples were taken at 0 minutes, 20 minutes, 1 hour or 3 hours after phage addition, washed as described in FIG. 4 including the trypsinization step and intracellular phages titered.

FIG. 5 shows the effect of phage concentration on the recovery of intracellular phage. Various concentrations of C6.5 scFv phagemid, C6ML3-9 scFv phagemid, C6.5 diabody phagemid or C6.5 scFv phage (input phage titer) were incubated with subconfluent SKBR3 cells grown in 6-well plates for 2 hours at 37° C. Cells were treated as described in FIG. 4 including the trypsinization step and intracellular phage were titered (output phage titer).

FIG. 6 illustrates strategies for producing anti-ErbB2 phagemids and phages packaging a eukaryotic reporter gene. Left column: Helper phage are used to infect TG1 containing pHEN-F5-GFP, a phagemid composed of an f1 origin of replication (f1 ori), the anti-ErbB2 F5 scFv gene fused to gene III and an eukaryotic GFP reporter gene driven by the CMV promoter. Phage recovered from the culture supernatant display an average of 1 scFv-pIII fusion protein and 99% of them package the GFP reporter gene. Right column: the anti-ErbB2 F5 scFv gene is cloned into the fd phage genome for expression as a scFv-pIII fusion. fd-F5 phages are used to infect TG1 containing a GFP reporter phagemid vector (pcDNA3-GFP). Phages purified from the culture supernatant display multiple scFv-pIII fusion protein and approximately 50% package the GFP reporter gene.

FIG. 7 shows a comparison of anti-ErbB2 phagemid and phage binding on cells. $10^5$ ErbB2 expressing SKBR3 cells were incubated with increasing concentrations of F5-phagemids (circles) or fd-F5-phages (squares) at 4° C. for 1 hour. Cell surface bound phages were detected with biotinylated anti-M13 and streptavidin-PE. Binding was detected by FACS and the results expressed as mean fluorescent intensity (MFI).

FIGS. 8A and 8B illustrate phagemid-mediated gene transfer in breast cancer cell lines. (FIG. 8A) (1, 2, 3) $2.0 \times 10^5$ MCF7 (low ErbB2 expression) or (4, 5, 6) $2.0 \times 10^5$ SKBR3 (high ErbB2 expression) cells grown in 6-well plates were incubated with either no (1,4) no phage, (2, 5) $5.0 \times 10^{12}$ cfu/ml of helper phage packaging GFP or (3, 6) $5.0 \times 10^{11}$ cfu/ml of F5-GFP-phagemids for 48 hrs. Cells were trypsinized and GFP detected by FACS. (FIG. 8B) An equal number of MCF7 and SKBR3 cells ($1.0 \times 10^5$) were grown together and incubated with $5.0 \times 10^{11}$ cfu/ml of F5-GFP-phagemids for 48 hrs. Cells were trypsinized and stained for ErbB2 expression using 4D5 antibody and rhodamine conjugated sheep anti-mouse Ig to discriminate SKBR3 (Region R1) and MCF7 (Region R2) cells. The GFP content of each subpopulation was determined by FACS.

FIGS. 9A, 9B, 9C, and 9D show concentration dependence and time course of phagemid mediated GFP expression in SKBR3 cells. FIGS. 9A and 9B show concentration dependence of phagemid and phage mediated GFP expression in SKBR3 cells. $5.0 \times 10^4$ cells were grown in 24-well plates and incubated with increasing concentrations of F5-GFP-phagemid (squares), fd-F5-GFP-phage (diamonds) or GFP-helper phage (circles). After 60 hrs, the cells were trypsinized and analyzed by FACS for GFP expression. FIGS. 9C and 9D show the time dependence of phagemid mediated GFP expression in SKBR3 cells. $5.0 \times 10^4$ cells were incubated with $5.10^{11}$ cfu/mL of F5-GFP-phagemid and analyzed for GFP expression by FACS. For incubation times greater than 48 hrs, the phage were added to $2.5 \times 10^4$ cells and the culture medium was replaced by fresh medium after 48 hrs of incubation. The results are expressed as (9A, 9C) % of GFP positive cells and (9B, 9D)) MFI of the GFP positive cells.

DETAILED DESCRIPTION

Figure 2A:
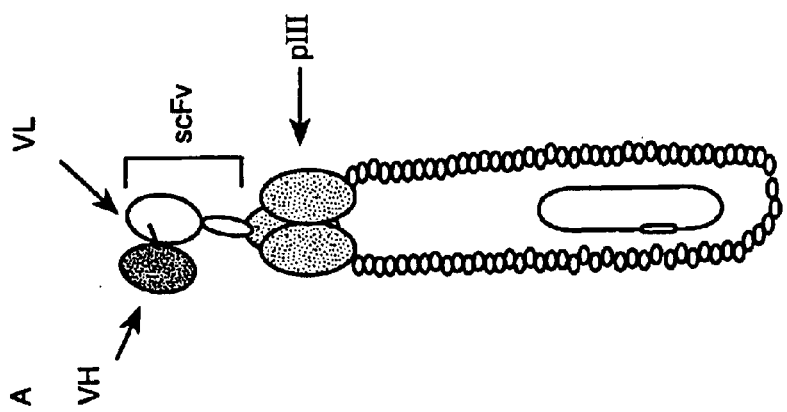
FIGS. 2A 2B, and 2C show schematics illustrating antibody phage display: Cartoon of phage displaying (2A) a single scFv (2B) a single diabody or (2C) multiple scFv. scFv=single chain Fv antibody fragment; $V_H$=Ig heavy chain variable domain; $V_L$=Ig light chain variable domain; pIII=phage minor coat protein pIII; Ag=antigen bound by scFv.

I. Introduction.

This invention provides new methods of screening for specific binding polypeptides and/or antibodies that are internalized by particular target cells. Unlike prior art assay methods that simply detect binding to an external target on a cell (e.g. a receptor) the assays of this invention explicitly identify molecules that bind and are transported into the cell (i.e. into a vacuole and/or the endoplasmic reticulum and/or into the cytosol itself).

The utility of a number of specific antibodies, even those generally known to bind to internalizing receptors (e.g. c-erbB-2) has been limited by the frequent lack of internalization of the bound antibody or by unacceptably slow internalization rates. Such antibodies while useful for delivering moieties to the cell surface, have proven generally unsatisfactory of the delivery of effector molecules that must obtain entry into the cell for activity.

In contrast, the binding polypeptides and/or antibodies identified by the methods of this invention are rapidly internalized into the cell. They are thus extremely useful for delivering effector moieties into the target cell. Moreover, once an internalizing antibody or polypeptide is identified it can be used to re-probe one or more cells or cell lines to identify previously unknown internalizing cellular targets (e.g., receptors).

In addition, selecting for internalization also selects for biologic function. Many receptors (for example growth factor receptors) use internalization as a way of modulating and regulating the effect of ligands. For example, ligand binding can result in signal transduction and receptor internalization. The decrease in the number of receptors then causes down regulation of the effect of additional ligand. The same occurs with antibodies that bind growth factor receptors (Hurwitz et al. (1995) *Proc. NatL. Acad. Sci. USA*. 92: 3353–3357). For example, "[g]rowth factors act by binding to and activating the intrinsic catalytic activity of their cell surface receptors, thereby initiating a signaling cascade leading to the cellular response. Growth factor/receptor complexes are not static residents of the cell surface membrane but undergo endocytotic trafficking processes of internalization and sorting to recycling or degradation. Consequently, growth factors are depleted from the extracellular medium and their receptors undergo down-regulation. These trafficking processes, by virtue of their influence on the kinetics of signaling growth factor/receptor complexes, are important modulators of cell behavioral responses" (Reddy et al. (1996) *Nature Biotech.* 14: 1696–1699)

In the ErbB2 system, one mechanism by which ErbB2 binding antibodies inhibit growth is to cause receptor internalization and down regulation (Hurwitz et al. (1995) *Proc. Natl. Acad. Sci. USA.* 92: 3353–3357). It also may be possible to turn an internalizing antibody that binds a growth factor receptor and causes growth inhibition into a growth stimulatory antibody. For example, the mitogenic properties of EGF have been increased by lowering the affinity of EGF for the EGF receptor. The lower affinity EGF causes receptor signaling, but reduced internalization and down regulation than wild type EGF (presumably from the lower affinity) (Reddy et al. (1996) *Nature Biotech.* 14: 1696–1699). Thus lowering the affinity of a growth inhibiting internalizing antibody could turn it into a growth factor. Thus identification of internalizing antibodies can provide lead compounds/drugs for both growth inhibition and growth stimulation.

II. Methods of Identifying Internalizing Antibodies and/or Receptors.

A) Identification of Internalizing Polypeptides/Antibodies.

In one embodiment, this invention provides methods for identifying internalizing antibodies or polypeptides. The methods involve contacting a "target" cell with one or more members of a phage display library displaying an antibody or a binding polypeptide. The phage display library is preferably a multivalent phage display library and it is believed that this invention provides the first description of a multivalent antibody phage display library.

After a suitable incubation period, the cells are washed to remove externally bound phage (library members) and then internalized phage are released from the cells, e.g., by cell lysis. It was a discovery of this invention that the internalized phage are still viable (infectious). Thus the internalized phage in the cell lysate can be recovered and expanded by using the lysate containing internalized phage to infect a bacterial host. Growth of infected bacteria leads to expansion of the phage which can be used for a subsequent round of selection. Each round of selection enriches for phage which are more efficiently internalized, more specific for the target cell or have improved binding characteristics.

The phage display library is preferably contacted with a subtractive cell line (i.e. a subtractive cell line is added to the target cells and culture media) to remove members of the phage display library that are not specific to the "target" cell(s). The subtractive cell line is preferably added under conditions in which members of the phage display library are not internalized (e.g., at a temperature of about 4° C. to about 20° C., more preferably at a temperature of about 4° C.) so that non-specific binding members of the library are not internalized (sequestered) before they can be subtracted out by the subtractive cell line.

After subtracting out non-specific binding antibodies, the "target" cells are washed to remove the subtractive cell line and to remove non-specifically or weakly-bound phage."

The target cells are then cultured under conditions where it is possible for internalization to occur (e.g. at a temperature of about 35° C. to about 39° C., more preferably at a temperature of about 37° C.). The duration of the internalization culture period will determine the internalization speed of the antibodies (phage display members) for which selection takes place. With shorter internalization periods more rapid internalizing antibodies are selected while with longer internalization periods slower internalizing antibodies are selected. The internalization period is preferably less than about 120 minutes, more preferably less than about 60 minutes, and most preferably less than about 30 minutes or even less than about 20 minutes.

It is noted that during the internalization period the target cells are grown under conditions in which internalization can occur. For a number of cell lines, this involves culturing the cells adherently on culture plates.

After internalization has been allowed to occur the target cells are washed to remove non-internalized (e.g. surface-bound phage).

The cells can then be moved to clean media. In a preferred embodiment, where the cells are adherent, the cells are trypsinized to free the cells from the extracellular matrix which may contain phage antibodies that bind the extracellular matrix. Freeing the cells into solution permits more through washing and moving of the cells to a new culture flask will leave behind any phage that may have stuck to the tissue culture dish.

The cells can then be washed with a large volume of PBS and lysed to release the internalized phage which can then be expanded e.g. used to infect *E. coli* to produce phage for the next round of selection. It is noted that there is no need to actually visualize the internalized phage. Simple cell lysis and expansion of the formerly internalized phage is sufficient for recovering internalizing phage display members.

B) Identification of Internalizing Receptors.

Once an antibody or polypeptide that is internalized into a cell has been identified, it is possible to probe one or more cell types with the identified antibody or polypeptide to identify the target recognized and bound by the antibody. Since the antibody is an internalizing antibody it is likely that such targets are themselves internalizing targets (e.g. members or portions of internalizing receptors).

In one embodiment, the antibody can be labeled as described below. The cells can then be contacted with the antibody (i.e. in vivo or in vitro) and the cells or cellular regions to which the antibody binds can then be isolated.

Alternatively, the antibodies can be used e.g. in an affinity matrix (e.g. affinity column) to isolate the targets (e.g. receptor or receptor subunits) to which they bind. Briefly, in one embodiment, affinity chromatography involves immobilizing (e.g. on a solid support) one or more species of the internalizing antibodies identified according to the methods of this invention. Cells, cellular lysate, or cellular homogenate are then contacted with the immobilized antibody which then binds to its cognate ligand. The remaining material is then washed away and the bound/isolated cognate ligand can then be released from the antibody for further use. Methods of performing affinity chromatography are well known to those of skill in the art (see, e.g., U.S. Pat. Nos.: 5,710,254, 5,491,096, 5,278,061, 5,110,907, 4,985, 144, 4,385,991, 3,983,001, etc.).

In another embodiment, the antibodies are used to immunoprecipitate the target from cell lysate. The precipitate is then run on an SDS-PAGE gel which is Western blotted onto nitrocellulose. The blot is probed with the precipitating antibody to identify the location of the target. The portion of the blot containing the target can then be sent for N-terminal protein sequencing. The N-terminal sequence can then be used to identify the target from standard databases, or DNA probes can be synthesized to probe genomic or cDNA libraries. This approach has been used to identify the antigen bound by a phage antibody. Selections of a phage antibody library were done on intact *Chlamydia trachomatis* (a bacterial like organism that causes Chlamydial diseases). Selected antibodies were then used as described above to identify the antigen bound.

C) Functional Genomics

In another embodiment, the assays of this invention can be used to screen libraries to identify previously unknown binding agents. There are two preferred approaches to this proteomic or functional genomic analysis. In the first, a phage displayed cDNA library is created. mRNA (probably subtracted) is made from the cell line or tissue of interest. First strand DNA is synthesized and treated with DNAse or fragmented in some other way. This removes the 5' and 3' UTR and the 3' stop codon. A phage library is then produced and selected for internalization on cells.

Ligands (or domains of ligands) that bind to cell surface receptors and internalized are identified. This approach might be used, for example, to identify orphan growth factors which bind to internalizing growth factor receptors. If a receptor is known, but the ligand is not, the receptor gene could be transfected into a cell line and the transfected cell line used for selection. The selection could also be combined with delivery of a reporter gene. In this case, the phage vector that is used to create the phage library would contain the reporter gene. After selection, one could isolate for example, green cells expressing the reporter gene GFP by FACS (rather than lysing all cells to recover internalized phage). This is expected to improve the specificity of selection For the second approach, second paragraph: the phage library is selected for internalization on a target cell line as described above. The selected polyclonal or monoclonal phage are then used to flow sort cells (e.g. COS cells) transfected with a cDNA library. cDNA library plasmids are recovered from sorted cells and amplified in bacteria using standard techniques. The amplified plasmid cDNA library is used to transfect cells (e.g., COS cells) which are again sorted using phage. After several rounds of selection, sorted cells should contain only plasmids encoding cell surface receptors bound by internalizing phage. These can be identified by DNA sequencing, and by testing each plasmid cDNA for binding of phage after the plasmid DNA is used to transfect COS cells.

III. Assay Components

A) Phage Display Library.

1) Mono-valent Antibody Libraries and Polypeptide Libraries.

The ability to express polypeptide and antibody fragments on the surface of viruses which infect bacteria (bacteriophage or phage) makes it possible to isolate a single binding polypeptide or antibody fragment from a library of greater than $10^{10}$ nonbinding clones. To express polypeptide or antibody fragments on the surface of phage (phage display), a polypeptide or an antibody fragment gene is inserted into the gene encoding a phage surface protein (pIII and the antibody fragment-pIII fusion protein is displayed on the phage surface (McCafferty et al. (1990) *Nature,* 348: 552–554; Hoogenboom et al. (1991) *Nucleic Acids Res.* 19: 4133–4137). Since the antibody fragments on the surface of the phage are functional, phage bearing antigen binding polypeptides or antibody fragments can be separated from non-binding phage by antigen affinity chromatography (McCafferty et al (1990) *Nature,* 348: 552–554). Depending on the affinity of the antibody fragment, enrichment factors of 20 fold-1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al (1990) *Nature,* 348: 552–554). Thus even when enrichments are low (Marks et al. (1991) *J. Mol. Biol.* 222: 581–597), multiple rounds of affinity selection can lead to the isolation of rare phage. Since selection of the phage antibody library on antigen results in enrichment, the majority of clones bind antigen after four rounds of selection. Thus only a relatively small number of clones (several hundred) need to be analyzed for binding to antigen.

In a preferred embodiment, analysis for binding is simplified by including an amber codon between the antibody fragment gene and gene III. The amber codon makes it possible to easily switch between displayed and soluble (native) antibody fragment simply by changing the host bacterial strain (Hoogenboom et al. (1991) *Nucleic Acids Res.* 19: 4133–4137).

Human antibodies can be produced without prior immunization by displaying very large and diverse V-gene repertoires on phage (Marks et al. (1991) J. Mol. Biol. 222: 581–597). In the first Example, natural $V_H$ and $V_L$ repertoires present in human peripheral blood lymphocytes were isolated from unimmunized donors by PCR. The V-gene repertoires were spliced together at random using PCR to create a scFv gene repertoire which was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol Biol.* 222: 581–597; Marks et al. (1993). *Bio/Technology.* 10: 779–783; Griffiths et al. (1993) *EMBO J.* 12: 725–734; Clackson et al. (1991) *Nature.* 352: 624–628). Antibodies have been produced against self proteins, including human thyroglobulin, immunoglobulin, tumor necrosis factor and CEA (Griffiths et al. (1993) *EMBO J.* 12: 725–734). It is also possible to isolate antibodies against cell surface antigens by selecting directly on intact cells. For example, antibody fragments against four different erythrocyte cell surface antigens were produced by selecting directly on erythrocytes (Marks et al. (1993). *Bio/Technology.* 10: 779–783). Antibodies were produced against blood group antigens with surface densities as low as 5,000 sites/cell. The antibody fragments were highly specific to the antigen used for selection, and were functional in agglutination and immunofluorescence assays. Antibodies against the lower density antigens were produced by first selecting the phage antibody library on a highly related cell type which lacked the antigen of interest. This negative selection removed binders against the higher density antigens and subsequent selection of the depleted phage antibody library on cells expressing the antigen of interest resulted in isolation of antibodies against that antigen. With a library of this size and diversity, at least one to several binders can be isolated against a protein antigen 70% of the time. The antibody fragments are highly specific for the antigen used for selection and have affinities in the 1:M to 100 nM range (Marks et al. (1991) *J. Mol. Biol.* 222: 581–597; Griffiths et al. (1993) *EMBO J.* 12: 725–734). Larger phage antibody libraries result in the isolation of more antibodies of higher binding affinity to a greater proportion of antigens.

The creation of a suitable large phage display antibody library is described in detail in Example 1.

2) Polyvalent Antibody Phage Display Libraries

The probability of selecting internalizing antibodies from a phage-display antibody library is increased by increasing the valency of the displayed antibody. This approach takes advantage of normal cell-surface receptor biology. Often cell-surface receptors (e.g. growth factor receptors) activate upon binding their cognate ligand through a process of homo- or heterodimerization (or trimerization, or tetramerization, etc.). The association of the receptor subunits in this process can be mediated directly (e.g. when bound by a bivalent ligand) or indirectly by causing a conformational change in the receptor.

It was a discovery of this invention that polyvalent antibodies in a display library (e.g. a phage display library) can mimic this process, stimulate endocytosis, become internalized and deliver their payload into the cytosol. Thus, to increase the likelihood of identifying internalizing antibodies or recognizing internalizing epitopes, preferred embodiments of this invention utilize a polyvalent phage display antibody library. It is believed that no multivalent phage-display antibody libraries have been created prior to this invention. Unlike the multivalently displayed peptide phage libraries, phage antibody libraries typically display monomeric single chain Fv (scFv) or Fab antibody fragments fused to pIII as single copies on the phage surface using a phagemid system (Marks et al. (1991) *J. Mol. Biol.* 222: 581–597; Sheets et al. (1998) *Proc. Natl. Acad. Sci. USA* 95: 6157–6162.).

As used herein, a polyvalent phage display antibody library, refers to a library in which each member (e.g. phage particle) displays, on average) two or more binding domains, wherein each binding domain includes a variable heavy and a variable light region. More generally, a multivalent phage display library displays, on average, two or more pIII fusions per page particle. Polyvalent phage display can be achieved by expressing diabodies (i.e., a protein formed by fusion or conjugation of two single chain antibodies (e.g. scFv)) or by display of, on average, two or more antibodies on each phage particle. In contrast, a mono-valent library displays, on average, one single-chain antibody per viral particle.

a) Diabody Expression.

Diabodies are scFv dimers where each chain consists of heavy ($V_H$) and light ($V_L$) chain variable domains connected using a linker (e.g. a peptide linker) that is too short to permit pairing between domains on the same chain. Consequently, pairing occurs between complementary domains of two different chains, creating a stable noncovalent dimer with two binding sites (Holliger et al. (1993) *Proc. NatL. Acad. Sci.* 90: 6444–6448). The C6.5 diabody was constructed by shortening the peptide linker between the Ig $V_H$ and $V_L$ domains from 15 to 5 amino acids and binds ErbB2 on SKBR3 cells bivalently with a $K_d$ approximately 40 fold lower than C6.5 ($4.0\times10^{-10}$ M) (Adams et aL (1998) *Brit. J Cancer.* 77: 1405–1412, 1998).

In Example 5, described herein, C6.5 diabody genes were subcloned for expression as pIII fusions in the phagemid pHEN-1 (Hoogenboom et al. (1991) *Nucleic Acids Res.* 19: 4133–4137). This yielded phagemid predominantly expressing a single scFv or diabody-pIII fusion after rescue with helper phage (Marks et al. (1992) *J. Biol. Chem.* 267: 16007–16010). Diabody phagemid display a bivalent antibody fragment resulting from intermolecular pairing of one scFv-pIII fusion molecule and one native scFv molecule. Using the teachings provided herein one of skill in the art can routinely produce other diabodies.

Phage displaying bivalent diabodies or multiple copies of scFv were more efficiently endocytosed than phage displaying monomeric scFv and recovery of infectious phage was increased by preincubation of cells with chloroquine.

The results indicate that it is possible to select for endocytosable antibodies, even at the low concentrations that would exist for a single phage antibody member in a library of $10^9$ members.

b) Polyvalent Display of Single-chain Antibodies.

As an alternative to the use of diabodies, antibody phage display libraries are created in which each viral particle, on average, expresses at least 2, preferably at least 3, more preferably at least 4, and most preferably at least 5 copies of a single chain antibody.

In principle, each copy of pIII on the page (and there is controversy as to whether there are 3 or 5 copies of pIII per phage) should express an antibody. However, proteolysis occurs and the number actually displayed is typically less. Thus, preferred multivalent antibody libraries are constructed in a phage vector and not a phage mid vector. This means that helper phage need not be added to make phage. Helper phage bring into the *E. coli* wild-type pIII that competes with the scFv-pIII fusion. Thus, in phagemid vector, this competition leas, on average, to only 1 (ore less) antibody per phage.

To produce multivalent antibody libraries, the single chain antibodies, typically expressed in phagemid, are subcloned from the phagemid vector into a phage vector. No helper phage is required and there is no competition between the wild-type pIII and the fusion scFv pIII fusion. thus, on average, the phage display two or more pIII fusions. Thus, by way of illustration, Example 5 describes the subcloning of the C6.5 scFv gene into the phage vector fd-Sfi/Not. This results in phage with 3 to 5 copies each of scFv-pIII fusion protein.

B) Target cells.

The target cells of this invention include any cell for which it is desired to identify an internalizing polypeptide or antibody or for which it is desired to identify an internalizing marker (e.g. receptor). The cells can include cells of multicellular eukaryotes, uni-cellular eukaryotes, including plants and fungi, and even prokaryotic cells. Preferred target cells are eukaryotic, more preferably vertebrate cells, and most preferably mammalian cells (e.g. cells from murines, bovines, primates including humans, largomorphs, canines, felines, and so forth). The cells can be normal healthy cells or cells characterized by a particular pathology (e.g. tumor cells).

Target cells can include any cell type where it would be useful to: 1) have an antibody specifically recognize the cell type or related cell types (for example for cell sorting, cell staining or other diagnostic procedures); 2) have a ligand which is specifically internalized into the cell type or related cell types (for example to deliver a toxic or therapeutic gene or protein). Additional target cells include, but are not limited to differentiated cells (i.e. differentiated to become a tissue, e.g. prostate, breast). Thus an antibody that recognized and killed prostate cells would be good for prostate cancer even if it killed normal prostate cells (the prostate is not an essential organ). Target cells may include tissue specific cells, and cells at a given developmental stage. Target cells may also include precursor cells, e.g. bone marrow stem cells, would be useful for isolating, perhaps stimulating for differentiation.

Target cells can also include cell lines transfected with a gene for a known receptor (for example ErbB2) to which it would be useful to have internalizing antibodies.

Many ErbB2 antibodies are not internalizing. Rather than immunizing with recombinant protein or selecting a phage library on recombinant protein, selection on ErbB2 transfected cells for internalization should yield precisely antibodies with the desired characteristics (internalization). Finally, a cDNA library could be transfected into a cell line (for example COS) from a desired target cell line or tissue and phage antibodies selected for internalization. After several rounds of selection, the phage could be used to stain and sort (for example by FACS) transfected cells. DNA can be recovered from the cells, yielding the sequences of internalizing receptors as well as phage antibodies that bind them.

C) Cells of a Subtractive Cell Line.

In a preferred embodiment of the assays of this invention, the phage display library is contacted with cells from a "subtractive" cell line. This step is intended to deplete or eliminate members of the phage display library that either bind the cells non-specifically or that bind to targets other than the target against which it is desired to obtain a binding polypeptide or antibody. The contacting with the cells from a "subtractive" cell line can occur before, during, or after the target cells are contacted with members of the phage display library. However, in a preferred embodiment, the contacting with cells of a subtractive cell line is simultaneous with contacting of the target cells. Thus, for example, in a preferred embodiment the target cell line (grown adherent to a tissue culture plate) is co-incubated with the subtracting cell line (in suspension) in a single cell culture flask.

Virtually any cell can act as a subtractive cell. However, in a preferred embodiment, subtractive cells display all the markers on the target cell except the marker (e.g. receptor) that is to act as a target for selection of the desired binding antibodies or binding polypeptides. Particularly preferred cells are thus closely related to the target cell(s), in terms of having common internalizing cell surface receptors (such as transferring for example fibroblasts. If one was selecting on a tumor cell line (for example a breast tumor cell line), than one could negatively select on a normal breast cell line. This may, however, deplete for antibodies that bind to overexpressed antigens, so again a parallel path would be to negatively select on fibroblasts. If one was using transfected cells, than non-transfected cell could be used as the subtractive cell line. Where the tumor is epithelial in origin, the preferred subtractive cell will also be epithelial and even more preferably from the same tissue or organ.

Particularly preferred subtractive cells include, but are not limited to, non-differentiated cell lines, non-transfected cells, mixtures of non-differentiated and non-transfected cells. When selecting for internalization on tumor cells, preferred subtractive cell lines are preferably the non-tumor cells of the same tissue (for example, breast tumor cells versus normal breast epithelial cells). Also, for cDNA expression libraries, the subtractive cell line will be the non-transformed cell line used for library construction (e.g. COS, CHO, etc.).

In one particularly preferred embodiment, the "target" cell is a cell transformed with a gene or cDNA for a specific target receptor. In this instance, the subtractive cell line is preferably the non-transformed cell line. Thus for example where CHO cells are transformed with a vector containing the gene for the EGF receptor, the EGF-expressing cells are used as the target cell line, and the subtractive cell line is the untransformed CHO cells. Using this approach internalizing anti-EGF receptor antibodies were obtained.

The subtractive cells are more effective when provided in excess over the target cells. The excess is preferably at least about a 2-fold to about a 1000-fold excess, more preferably about a 3-fold to about a 100-fold excess, and most preferably about a 5-fold to about a 50-fold excess. In one embodiment, a 5-fold excess is sufficient.

D) Washing Steps.

As indicated above a variety of washing steps are used in the methods of this invention. In particular, a "weak" washing step can be used to remove the subtractive cells and weakly or non-specifically binding members of the phage display library. A second strong washing step is preferably used after internalization of members of the phage display library. The "strong" washing step is intended to remove tightly- and weakly-bound surface phage.

Buffers and methods for performing weak and strong wash steps are well known to those of skill in the art. For example, weak washes can be done with standard buffers or culture media (e.g., phosphate buffered saline (buffer) DMEM (culture media), etc.).

E Culturing Under Internalizing Conditions.

As explained above, the cells are preferably cultured under "internalizing" conditions. Internalizing culture conditions are conditions in which the cell when bound by a member of a phage display library at an appropriate (e.g. internalizing) site or receptor, transports the bound member into the cell. This can involve transport into a vesicle, into the endoplasmic reticulum, the golgi complex, or into the cytosol of the cell itself.

Internalizing conditions are most easily achieved when the cells are cultured under conditions that mimic those of the cell in its native state. Thus many cells, e.g. epidermal cells, preferably grow ad adherent layers attached to a basement membrane. Such cells more effectively internalize binding polypeptides and antibodies when they are cultured as adherent monolayers.:Chloroquine and serum free medium both avoid non specific internalization and enhance specific internalization (ligands in the serum that induce the internalization of receptor of interest and take with them non specific phages being in the neighborhood). In addition, for internalization to occur, the cells should be cultured at a temperature and pH that permits internalization. Suitable temperature and pH range from about 35° C. to about 39° C. and from pH 6 to about pH 8, more preferably from about pH 6.5 to about pH 7.5, with preferred temperature and pH being about 37° C. and pH 7.5 respectively. In a preferred embodiment, the cells are preincubated in serum culture medium for about two hours before adding the phages and the competitor (subtraction) cells.

F) Identification of Internalized Phage

The internalized phage display library members can be identified directly or indirectly. Direct identification can be accomplished simply by visualizing the phage within a cell e.g. via immunofluorescent or confocal microscopy. Phage internalization can be identified by their ability to deliver a reporter gene that is expressed within the cell. The reporter gene can be one that produces a detectable signal (e.g. a fluorescent (e.g. lux, green fluorescent protein, etc.) or colorimetric signal (e.g. HRP, β-galactosidase) or can itself be a selectable marker (e.g. an antibiotic resistance gene).

The use of both β-galactosidase and GFP as reporter genes in such phage is described herein.

Alternatively, the phage display member can bear a marker (e.g. a label) and cells containing the internalized phage can be detected simply by detection of the label (e.g. in a flow cytometer). The direct methods preferably used for identification of the receptors or cells that are bound after selections are performed. It is noted that cell sorting approaches (FACs) will work with identification of either surface bound or internalized phage. However, an additional level of specificity can be achieved if the cells are first sorted for the presence of internalized phage prior to lysis. Direct methods are also used during the analysis phase to demonstrate that the phage selected are indeed internalized.

Alternatively the internalized phage display library members can be identified indirectly. In indirect detection methods the phage-display library member(s) do not need to be detected while they are present within the cell. It is sufficient that they simply have been internalized.

Indirect identification is accomplished for example, by isolating and expanding the phage that were internalized into the cells as described below. Indirect identification is particularly well suited where the identified phage display library members are going to be used in subsequent rounds of selection or to isolate bacteria harboring monoclonal phage genomes for subsequent monoclonal phage characterization (that is for the analysis of selection results).

G) Isolation and Expansion of Internalized Phage.

It was a discovery of this invention that phage display library members that have been internalized into target cells (e.g. mammalian tumor cells) remain viable and can be recovered and expanded into a "selected" library suitable for subsequent rounds of selection and/or isolation and characterization of particular members.

As used herein, the term "recovery" is intended to include recovery of the infectious phage and/or recovery of the phage antibody gene and/or recovery of a heterologous nucleic acid accompanying the antibody gene.

The internalized phage can be isolated and expanded using standard methods. Typically these include lysing the cells (e.g., with 100 mM triethylamine (high pH)), and using the lysate to infect a suitable bacterial host, e.g., *E. coli* TG1. The phage-containing bacteria are then cultured according to standard methods (see, e.g., Sambrook supra., Marks et al. (1991) *J. Mol. Biol.* 222: 581–597).

IV. Preparation and Modification of Internalizing antibodies.

As described below, once an internalizing antibody is identified additional copies of the antibody can be prepared using either chemical synthetic means or by the use of recombinant expression systems. In addition, other "related" internalizing antibodies can be identified by screening for antibodies that bind to the same epitope and/or by modification of the identified internalizing antibody to produce libraries of modified antibody and then rescreening antibodies in the library internalization.

A) Antibody Synthesis.

1) Chemical Synthesis.

The internalizing antibodies, once identified by the methods of this invention, can be chemically synthesized using well known methods of peptide synthesis. Solid phase synthesis in which the C-terminal amino acid of the sequence is attached to an insoluble support followed by sequential addition of the remaining amino acids in the sequence one preferred method for the chemical synthesis of single chain antibodies. Techniques for solid phase synthesis are described by Barany and Merrifield, *Solid Phase Peptide Synthesis*; pp. 3–284 in *The Peptides: Analysis, Synthesis,*

*Biology.* Vol. 2: *Special Methods in Peptide Synthesis*, Part A., Merrifield et al. (1963) *J. Am. Chem. Soc.*, 85: 2149–2156, and Stewart et al. (1984) *Solid Phase Peptide Synthesis*, 2nd ed. Pierce Chem. Co., Rockford, Ill.

2) Recombinant Expression of Internalizing Antibodies.

In a preferred embodiment, the internalizing antibodies, once identified by the methods of this invention, are prepared using standard techniques well known to those of skill in the art. Nucleic acid sequences encoding the internalizing antibodies are determined (e.g. via Sanger sequencing). Using the sequence information, the nucleic acids may be chemically synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12: 6159–6168) or manually synthesized using the solid phase phosphoramidite triester method described by Beaucage et. al. (Beaucage et. al. (1981) *Tetrahedron Letts.* 22(20): 1859–1862). Alternatively, nucleic acids encoding the antibody can be amplified and/or cloned according to standard methods.

Molecular cloning techniques to achieve these ends are known in the art. A wide variety of cloning and in vitro amplification methods suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl Acad. Sci. USA* 86: 10029–10033. In addition, detailed protocols for the isolation and cloning of the antibody are provided herein in the Examples, and in Schier et al. (1996) *J. Mol. Biol.*, 263: 551–567.

B) Identification of Other Antibodies Binding the Same "Internalizing" Epitope.

Once one or more internalizing antibodies are identified by the screening methods of this invention, other "related" internalizing antibodies can be identified by screening for antibodies that cross-react with the identified internalizing antibodies, either at the epitope bound by the antibodies or with an idiotypic antibody raised against the internalizing antibodies.

1) Cross-reactivity with Anti-Idiotypic Antibodies.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of internalizing antibodies identified in the screening systems of this invention using standard methods well known to those of skill in the art. Briefly, anti-idiotype antibodies can be made by injecting internalizing antibodies of this invention, or fragments thereof (e.g., CDRs)) into an animal thereby eliciting antiserum against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1)spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine). In general, it is desirable to use a myeloma cell line which does not secrete an immunoglobulin. Several such lines are known in the art. A preferred cell line is P3X63Ag8.653. This cell line is on deposit at the American Type Culture Collection as CRL-1580.

Fusion can be carried out in the presence of polyethylene glycol according to established methods (see, e.g., *Monoclonal Antibodies*, R. Kennett, J. McKearn & K. Bechtol, eds. N.Y., Plenum Press, 1980, and *Current Topics in Microbiology & Immunology*, Vol. 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10–14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

2) Cross-Reactivity with the F5 or C1 Epitope.

Instead of the anti-idiotypic antibody, other internalizing antibodies can be identified by cross-reactivity with the identified "prototypic" antibodies, against the epitope(s) used in the original selection. Competition between the "prototypic" internalizing antibodies and new candidates in an epitope-mapping format establishes that the antibodies are competing for the same epitope.

C) Phage Display Methods to Select Other "Related" Internalizing Antibodies.

1) Chain Shuffling Methods.

To create higher affinity antibodies, mutant scFv gene repertories, based on the sequence of a binding of an identified internalizing antibody, are created and expressed on the surface of phage. Higher affinity scFvs are selected on antigen as described above and in the Examples.

One approach to creating modified single-chain antibody (scFv) gene repertoires has been to replace the original $V_H$ or $V_L$ gene with a repertoire of V-genes to create new partners (chain shuffling) (Clackson et al. (1991) Nature. 352: 624–628). Using chain shuffling and phage display, the affinity of a human scFv antibody fragment which bound the hapten phenyloxazolone (phOx) was increased from 300 nM to 1 nM (300 fold) (Marks et al. (1992) Bio/Technology 10: 779–783).

Thus, for example, to alter the affinity of an internalizing antibody, a mutant scFv gene repertoire can be created containing the $V_H$ gene of the internalizing antibody and a human $V_L$ gene repertoire (light chain shuffling). The scFv gene repertoire can be cloned into the phage display vector pHEN-1 (Hoogenboom et al. (1991) Nucleic Acids Res., 19: 4133–4137) and after transformation a library of transformants is obtained.

Similarly, for heavy chain shuffling, the internalizing antibody $V_H$ CDR1 and/or CDR2, and/or CDR3 and light chain are cloned into a vector containing a human $V_H$ gene repertoire to create a phage antibody library transformants. For detailed descriptions of chain shuffling to increase antibody affinity see Schier et al. (1996) J. Mol. Biol., 255: 28–43, 1996.

2) Site-directed Mutagenesis to Improve Binding Affinity.

The majority of antigen contacting amino acid side chains are located in the complementarity determining regions (CDRs), three in the VH (CDR1, CDR2, and CDR3) and three in the VL (CDR1, CDR2, and CDR3) (Chothia et al. (1987) J. Mol. Biol., 196: 901–917; Chothia et al. (1986) Science, 233: 755–8; Nhan et al. (1991) J. Mol. Biol., 217: 133–151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) J. Mol. Biol., 234: 564–578; Wells (1990) Biochemistry, 29: 8509–8516). Site-directed mutagenesis of CDRs and screening against c-erbB-2 may be used to generate C6 antibodies having improved binding affinity and/or internalization of a known internalizing antibody.

3) CDR Randomization to Produce Higher Affinity Human scFv.

In an extension of simple site-directed mutagenesis, mutant antibody libraries can be created where partial or entire CDRs are randomized ($V_L$ CDR1 and CDR2 and $V_H$ CDR1, CDR2 and CDR3). In one embodiment, each CDR is randomized in a separate library, using the known internalizing antibody as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times b\ 10^{-10}$ to $9.0 \times 10^{-13}$ M (Lowman et al. (1993) J. Mol. Biol., 234: 564–578).

$V_H$ CDR3 often occupies the center of the binding pocket, and thus mutations in this region are likely to result in an increase in affinity (Clackson et al. (1995) Science, 267: 383–386). In one embodiment, four $V_H$ CDR3 residues are randomized at a time using the nucleotides NNS (see, e.g., Schier et al. (1996) Gene, 169: 147–155; Schier and Marks (1996) Human Antibodies and Hybridomas. 7: 97–105, 1996; and Schier et al. (1996) J. Mol. Biol. 263: 551–567, 1996).

4) Creation of Homodimers.

To create (scFv')$_2$ antibodies, two internalizing scFvs are joined, either through a linker (e.g., a carbon linker, a peptide, etc.) or through a disulfide bond between, for example, two cysteins. Thus, for example, to create disulfide linked scFv, a cysteine residue is introduced by site directed mutagenesis between the myc tag and a hexahistidine tag at the carboxy-terminus of the antibodies described herein. Introduction of the correct sequence can be verified by DNA sequencing. If the construct is in pUC119, the pe1B leader directs expressed scFv to the periplasm and cloning sites (Nco1 and Not1) exist to introduce F5 or C1 mutant scFv. The expressed scFv has the myc tag at the C-terminus, followed by 2 glycines, a cysteine, and then 6 histidines to facilitate purification by IMAC. After disulfide bond formation between the two cysteine residues, the two scFv are separated from each other by about 26 amino acids (two 11 amino acid myc tags and 4 glycines).

An scFv can be expressed from this construct, purified by IMAC, and analyzed by gel filtration. To produce (scFv')$_2$ dimers, the cysteine is reduced by incubation with 1 mM Ǝ-mercaptoethanol, and half of the scFv blocked by the addition of DTNB. Blocked and unblocked scFvs are incubated together to form (scFv')$_2$ and the resulting material can be analyzed by gel filtration. The affinity of the F5 and C1 scFv' monomers and the F5 and C1 (scFv')2 dimers is determined by BIAcore.

In a particularly preferred embodiment, the (scFv')$_2$ dimer is created by joining the scFv' fragments through a linker, more preferably through a peptide linker. This can be accomplished by a wide variety of means well known to those of skill in the art. For example, one preferred approach is described by Holliger et al. (1993) Proc. Natl. Acad. Sci. USA, 90: 6444–6448 (see also WO 94/13804).

5) Measurement of Antibody/Polypeptide Binding Affinity.

As explained above, selection for increased avidity involves measuring the affinity of the antibody for the target antigen (e.g., c-erbB-2). Methods of making such measurements are described in detail in copending application U.S. Ser. No. 08/665,202. Briefly, for example, the $K_d$ of F5, C1, or an F5- or C1-derived antibody the kinetics of binding to c-erbB-2 are determined in a BIAcore, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

V. Libraries and Vectors.

In another embodiment, this invention provides libraries and vectors for practice of the methods described herein. The libraries are preferably polyvalent libraries, including diabody libraries and more preferably including multi-valent single chain antibody libraries (e.g. scFv), (e.g., expressed by phage).

The libraries can take a number of forms. Thus, in one embodiment the library is a collection of cells containing members of the phage display library, while in another embodiment, the library consists of a collection of isolated phage, and in still library consists of a library of nucleic acids encoding a polyvalent phage display library. The nucleic acids can be phagemid vectors encoding the antibodies and ready for subcloning into a phage vector or the nucleic acids can be a collection of phagemid already carrying the subcloned antibody-encoding nucleic acids.

VI. Kits For Selecting Internalizing Antibodies.

In another embodiment, this invention provides kits for practice of the methods described herein. The kits preferably include members of a phage display library (e.g., as phage particles, as vectors, or as cells containing phage). The assay kits can additionally include any of the other components described herein for the practice of the assays of this invention. Such materials preferably include, but are not limited to, helper phage, one or more bacterial or mammalian cell lines, buffers, antibiotics, labels, and the like.

In addition the kits may optionally include instructional materials containing directions (i.e., protocols) disclosing the selection methods described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Creation of a non-immune Human Fab Phage Antibody Library Containing $10^9$–$10^{11}$ Members Manipulation of previous $10^7$ member phage display libraries revealed two major limitations: 1) expression levels of Fabs was too low to produce adequate material for characterization, and 2) the library was relatively unstable. These limitations are a result of creating the library in a phage vector, and the use of the cre-lox recombination system. We therefore decided that the best approach for this project was to create a very large scFv library using a phagemid vector. The goal was to produce a library at least 100 times larger than our previous $3.0 \times 10^7$ member scFv library. The approach taken was to clone the $V_H$ and $V_L$ library on separate replicons, combine them into an scFv gene repertoire by splicing by overlap extension, and clone the scFv gene repertoire into the phage display vector pHEN1. Human peripheral blood lymphocyte and spleen RNA was primed with IgM heavy chain constant region and, kappa and lambda light chain constant region primers and first strand cDNA synthesized. 1st strand cDNA was used as a template for PCR amplification of VH Vκk and Vλ gene repertoires.

The $V_H$ gene repertoires were cloned into the vector pUC119Sfi-Not as NcoI-NotI fragments, to create a library of $8.0 \times 10^8$ members. The library was diverse by PCR fingerprinting. Single chain linker DNA was spliced onto the $V_L$ gene repertoires using PCR and the repertoire cloned as an XhoI-NotI fragment into the vector pHENIXscFv to create a library of $7.2 \times 10^6$ members. The $V_H$ and $V_L$ gene repertoires were amplified from their respective vectors and spliced together using PCR to create an scFv gene repertoire. The scFv gene repertoire was cloned as an NcoI-NotI fragment into the vector to create an scFv phage antibody library of $7.0 \times 10^9$ members. The library was diverse as determined by BstN1 fingerprinting.

To verify the quality of the library, phage were prepared and selected on 14 different protein antigens. The results are shown in Table 1. scFv antibodies were obtained against all antigens used for selection, with between 3 and 15 unique scFv isolated per

TABLE 1

Results of phage antibody library selections. For each antigen (column 1), the number and the percentage of positive clones selected (column 2) and the number of different antibodies isolated (column 3) is indicated

| Protein antigen used for selection | Percentage (number) of ELISA positive clones | Number of different antibodies isolated |
|---|---|---|
| FGF Receptor ECD | 69 (18/26) | 15 |
| BMP Receptor Type I ECD | 50 (12/24) | 12 |
| Activin Receptor Type I ECD | 66 (16/24) | 7 |
| Activin Receptor Type II ECD | 66 (16/24) | 4 |
| Erb-B2 ECD | 91 (31/34) | 14 |
| VEGF | 50 (48/96) | 6 |
| BoNT/A | 28 (26/92) | 14 |
| BoNT-A C-fragment | 95 (87/92) | 10 |
| BoNT/B | 10 (9/92) | 5 |
| BoNT/C | 12 (11/92) | 5 |
| BoNT/E | 9 (8/92) | 3 |
| Bungarotoxin | 67 (64/96) | 15 |
| Cytochrome b5 | 55 (53/96) | 5 |
| Chlamydia trachomatis EB | 66 (63/96) | 7 | antigen (average 8.7) (Table 1). This compares favorably to results obtained from smaller scFv libraries (1 to a few binders obtained against only 70% of antigens used for selection). Affinities of 4 anti-ErbB-2 scFv and 4 anti-Botulinum scFv were measured using surface plasmon resonance in a BIAcore and found to range from $4.0 \times 10^{-9}$ M to $2.2\times10^{-10}$M for the anti-ErbB2 scFv and $2.6\times10^{-8}$M to $7.15\times10^{-8}$M for the anti-Botulinum scFv (Table 2). scFv were highly specific for the antigen used for selection (FIG. 2). The library could also be successfully selected on complex mixtures of antigen.

TABLE 2

Affinities and binding kinetics of anti-BoNT A C-fragment and anti-Erb-B2 scFv. Association ($k_{on}$) and dissociation ($k_{off}$) rate constants for purified scFvs were measured using surface plasmon resonance (BIAcore) and Kd calculated as ($k_{off}/k_{on}$).

| Specificity and clone | $K_d$ ($\times 10^{-9}$M) | $k_{on}$ ($\times 10^{-5}$M$^{-1}$s$^{-1}$) | $k_{off}$ ($\times 10^{-3}$s$^{-1}$) |
|---|---|---|---|
| ErbB-2 B7A | 0.22 | 4.42 | 0.1 |
| ErbB-2 G11D | 0.48 | 2.19 | 0.11 |
| ErbB-2 A11A | 0.49 | 3.69 | 0.18 |
| ErbB-2 F5A | 4.03 | 1.62 | 0.65 |
| BoNT-A 2A9 | 26.1 | 0.25 | 0.66 |
| BoNT-A 2H6 | 38.6 | 2.2 | 8.5 |
| BoNT-A 3F6 | 66.0 | 4.7 | 30.9 |
| BoNT-A 2B6 | 71.5 | 1.1 | 7.8 |

For example, selection on *Chlamydia trachomatis* elementary bodies (the causative organism of Chlamydial disease) yielded seven that specifically recognized chlamydia (Table 1). The scFv could be successfully used in a number of immunologic assays including ELISA, immunofluorescence, Western blotting, epitope mapping and immunoprecipitation. The number of binding antibodies for each antigen, and the affinities of the binding scFv are comparable to results obtained from the best phage antibody libraries (Table 3). Thus the library was established as a source of panels of human antibodies against any antigen with affinities at least equivalent to the secondary murine response.

TABLE 3

Comparison of protein binding antibodies selected from non-immune phage-display antibody libraries. *For library type, N = V-gene repertoires obtained from V-genes rearranged in vivo; SS = semi-synthetic V-genes constructed from cloned V-gene segments and synthetic oligonucleotides encoding $V_H$ CDR3. ND = not determined.

| Library | Library size and type* | Number of protein antigens studied | Average number of antibodies per protein antigen | Number of affinities measured | Range of affinities for protein antigens $K_d$ ($\times 10^{-9}$M) |
|---|---|---|---|---|---|
| Marks et al (1991) J. Mol. Biol. 222: 581–597 | $3.0 \times 10^7$ (scFv, N) | 2 | 2.5 | 1 | 100–2000 |
| Nissim et al (1994) EMBO J. 13: 692–698 | $1.0 \times 10^8$ (scFV, SS) | 15 | 2.6 | ND | ND |
| DeKruif et al (1995) J. Mol. Biol. 248: 97–105 | $3.6 \times 10^8$ (scFv, SS) | 12 | 1.9 | 3 | 100–2500 |
| Griffiths et al (1994) EMBO J. 13: 3245–3260 | $6.5 \times 10^{10}$ (Fab, SS) | 30 | 4.8 | 3 | 7–58 |
| Vaughan et al (1996) Nature Biotechnology, 14: 309–314 | $1.4 \times 10^{10}$ (scFv, N) | 3 | 7.0 | 3 | 4.2–8.0 |
| Present Examples | $6.7 \times 10^9$ (scFv, N) | 14 | 8.7 | 8 | 0.22–71.5 |

These experiments demonstrate the creation of a high complexity human scFv phage antibody library from which a panel of high affinity human scFv can be generated against any purified antigen. Such a library is ideal for probing the surface of cells to identify novel cell surface markers.

Example 2

Uptake of scFV into Cells by Receptor Mediated Endocytosis and Subsequent Recovery.

The $7.0\times10^9$ member scFv phage antibody library described above was selected on the malignant breast tumor cell lines MB231 and ZR-75-1, both with and without negative selections on the normal breast cell line HBL100. Similar results were obtained as described in section above. scFv were isolated that could not distinguish malignant from non-malignant cell lines.

To increase the specificity of selections, it was hypothesized that phage binding cell surface receptors could be taken up into cells by receptor mediated endocytosis and could then be recovered from cells by lysing the cells. This assumed: 1) that phage could be internalized by receptor mediated endocytosis and 2) that phage could be recovered in the infectious state from within cells prior to lysosomal degradation. The ability to select for internalized phage antibodies would have two major benefits: 1) the identification of antibodies that bind to receptors capable of internalization and 2) an added level of specificity in the selection process. Identification of antibodies which are internalized would be highly useful for many targeted therapeutic approaches where internalization is essential (e.g. immunotoxins, targeted liposomes, targeted gene therapy vectors and others).

A) Receptor Mediated Internalization of F5 or C1 Phase

To determine proof of principle, we utilized C6.5 phage and C6.5 diabody phage (see, copending application U.S. Ser. No. 08/665,202). We have previously shown that C6.5 scFv is internalized, but at a slow rate, and that the C6.5 diabody is somewhat better internalized (probably because it causes receptor dimerization). C6.5 phage, C6.5 diabody phage or an irrelevant anti-Botulinum phage were incubated with SKBR3 cells (ErbB2 expressing breast tumor cell line) at either 37° C. or 4° C. and non-internalized phage removed by sequential washing with PBS and low pH glycine buffer. The cells were then permeabilized and biotinylated anti- M13-antibody added followed by streptavidin Texas Red. Cells were then examined by using a confocal microscope. Both C6.5 phage and C6.5 diabody phage were observed within the cytoplasm). Approximately 1% of cells had internalized C6.5 phage and 20% of the cells had internalized C6.5 diabody phage. There was no internalization of the anti-Botulinum phage.

To determine if infectious phage could be specifically taken up and recovered from within cells, C6.5 phage or C6.5 diabody phage were incubated with SKBR3 cells at 37° C. Non bound phage were removed by washing with PBS and phage bound to the cell surface were eluted by washing twice with low pH glycine. The cells were then lysed and each fraction (the first and second glycine washes and the cytoplasmic fraction) used to infect E. coli TG1. Twenty times (C6.5) or 30 times (C6.5 diabody) more phage were bound to the cell surface than the anti-Botulinum phage (glycine 1 wash) (Table 4). After the second glycine wash, the titre of infectious phage from the cell surface decreased, indicating that washing was effective at removing surface bound phage (Table 4). After cell lysis, the titer increased more than 10 fold (C6.5 phage) or 50 fold (C6.5 diabody phage) from the second glycine wash. We believe this titre represents phage recovered from inside the cell. Recovery of phage from inside the cell was 100 times higher for ErbB2 binding C6.5 than for anti-Botulinum phage and 200 fold higher for C6.5 diabody phage (Table 4).

TABLE 4

Titer of cell surface bound phage and internalized phage.
$5.0 \times 10^{11}$ phage (anti-Botulinum or anti-ErbB2) were incubated with approximately $1.0 \times 10^5$ ErbB2 expressing SKBR3 cells at 37° C.. Cells were washed 10 times with PBS and surface bound phage eluted with two low pH glycine washes. The cells were then washed once with PBS and the cells lysed to release internalized phage. The phage titer was then determined for each of the glycine washes and for the lysed cell fraction by infection of E. coli TG1.

| Phage specificity | 1st glycine wash | 2nd glycine wash | Lysed cell fraction |
|---|---|---|---|
| anti-Botulinum | $6.0 \times 10^5$ | $1.0 \times 10^5$ | $6.0 \times 10^5$ |
| Anti-ErbB2 (C6.5 scFv) | $1.2 \times 10^7$ | $5.2 \times 10^6$ | $6.8 \times 10^7$ |
| Anti-ErbB2 (C6.5 diabody) | $1.8 \times 10^7$ | $2.8 \times 10^6$ | $1.7 \times 10^7$ |

Taken together, the results indicate that: 1) phage binding cell surface receptors can be taken up by cells and the infectious phage recovered from the cytoplasm. The amount of uptake is significantly greater than uptake of non-binding phage, and the 100 to 200 fold difference is well within the range that would allow enrichment from a library. What is unknown from the results is whether the phage antibodies are mediating receptor mediated internalization or whether they are merely taken up after binding by membrane turnover.

B) Selection and Characterization of Internalizing Antibodies from a Phage Antibody Library The results described above encouraged us to attempt selection of the phage antibody library described above to identify new phage antibodies that were internalized. Phage antibodies were rescued from the library and selected on SKBR3 cells. For selection, phage were incubated with cells at 37° C., non-binding phage removed by washing cells with PBS and phage bound to cell surface antigens removed by sequential washes with low pH glycine. Cells were then lysed to release internalized phage and the lysate used to infect E. coli TG1 to prepare phage for the next round of selection. Three rounds of selection were performed. One hundred clones from each round of selection were analyzed for binding to SKBR3 cells and to ErbB2 extracellular domain by ELISA. We hypothesized that we were likely to obtain binders to ErbB2 since SKBR3 cells are known to express high levels and ErbB2 is a receptor which is known to be internalized. After each round of selection, the titer of phage recovered from the cytoplasm increased (Table 5). After the third round, 45% of the clones were positive SKBR3 cell binding and 17% bound ErbB2 (Table 5).

TABLE 5

Results of selection of a phage antibody library for internalization. For each round of selection, the titer of phage in lysed cells, number of cells lysed and number of phage per cell is indicated. After the third round, individual clones were analyzed for binding to SKBR3 cells by ELISA and to ErbB2 ECD by ELISA.

| Round of selection | # of phage in cell lysate | # of cells lysed | # of phage/cell | % SKBR3 binders | % ErbB2 binders |
|---|---|---|---|---|---|
| 1 | $3.5 \times 10^4$ | $2.8 \times 10^6$ | 0.013 | ND | ND |
| 2 | $1.2 \times 10^5$ | $2.8 \times 10^6$ | 0.038 | ND | ND |
| 3 | $7.5 \times 10^6$ | $2.8 \times 10^6$ | 3.75 | 45% | 17% |

To estimate the number of unique binders, the scFv gene from ELISA positive clones was PCR amplified and fingerprinted by digestion with BstN1. Two unique restriction patterns were identified. The scFv genes were sequenced and 2 unique ErbB2 binding scFv identified. Similar analysis of SKBR3 ELISA positive clones that did not bind ErbB2 identified an additional 11 unique scFv.

To verify that phage antibodies were specific for SKBR3 cells, phage were prepared from each unique clone and analyzed for binding to SKBR3 cells (high ErbB2 expression) as well as 2 other epithelial tumor cell lines (SK-OV-3, moderate ErbB2 expression and MCF7, low ErbB2 expression) and a normal breast cell line (HS578B). Each unique clone specifically stained tumor cell lines but not the normal breast cell line.

SKBR3 and MCF7 cells were incubated with phage antibodies C6.5 (positive control), 3TF5 and 3 GH7. The latter two clones were isolated from the library, with 3TF5 binding ErbB2 and the antigen bound by 3 GH7 unknown. All 3 phage antibodies intensely stain SKBR3 cells (the selecting cell line and high ErbB2 expresser. C6.5 phage weakly stain MCF7 cells (low ErbB2 expressor). The anti-ErbB2 clone 3TF5 from the library stains MCF7 cells much more intensely then C6.5, as does 3 GH7.

SKBR3, SK-OV-3, MCF7 and HST578 cells were studied using native purified scFv 3TF5 and 3 GH7. For these studies, the scFv genes were subcloned into a vector which fuses a hexahistidine tag to the scFv C-terminus. scFv was then expressed, harvested from the bacterial periplasm and purified by immobilized metal affinity chromatography. The two scFv intensely stain SKBR3 cells, and do not stain the normal breast cell line HST578. There is minimal staining of the low ErbB2 expressing cell line MCF7 and intermediate staining of SK-OV-3 cells (moderate ErbB2 expresser). In general, the intensity of staining is less than seen with phage. This is to be expected since the secondary antibody for phage staining recognizes the major coat protein (2500 copies/phage) resulting in tremendous signal amplification.

The anti-ErbB2 phage antibody 3TF5 was studied further to determine if it was indeed internalized. This antibody was selected for initial study since its internalization could be compared to ErbB2 binding C6.5. $5.0 \times 10^{11}$ 3TF5 or C6.5 phage were incubated with SKBR3 cells at 37° C. or at 4° C. After washing with PBS, 3TF5 phage stained cells more intensely than C6.5 phage. After washing with low pH glycine, confocal microscopy revealed that 3TF5 phage were internalized by greater than 95% of cells, while C6.5 was internalized by only a few percent of cells. Incubation of either antibody at 4° C. led to no internalization.

The native purified 3TF5 scFv was similarly analyzed and was also efficiently internalized by SKBR3 cells. It should be noted that the native 3TF5 scFv existed only as a monomer with no appreciable dimerization or aggregation as determined by gel filtration.

These experiments demonstrate that phage antibodies can be internalized by cells and recovered from the cytoplasm. Phage that bind an internalizing cell surface receptor can be enriched more than 100 fold over non-binding phage. This level of enrichment is greater than that achieved by selecting on the cell surface. We have applied this approach to library selection and isolated phage antibodies that bind and are internalized by SKBR-3 cells. Several of these antibodies bind to ErbB2, but are more efficiently internalized than antibodies such as C6.5 that were generated by selecting on pure antigen. Many other antibodies have been isolated that bind specifically to SKBR-3 and other breast tumor cell lines and are efficiently internalized. These antibodies should prove useful for tumor targeting and for identifying potentially novel internalizing tumor cell receptors.

Example 3

Increasing the Affinity of Antibody Fragments with the Desired Binding Characteristics by Creating Mutant Phage Antibody Libraries and Selecting on the Appropriate Breast Tumor Cell Line Phage display has the potential to produce antibodies with affinities that cannot be produced using conventional hybridoma technology. Ultra high affinity human antibody fragments could result in excellent tumor penetration, prolonged tumor retention, and rapid clearance from the circulation, leading to high specificity. We therefore undertook a series of experiments to develop methodologies to generate ultra high affinity human antibody fragments. Experiments were performed to answer the following questions: 1) What is the most effective way to select and screen for rare higher affinity phage antibodies amidst a background of lower affinity binders; 2 What is the most effective means to remove bound phage from antigen, to ensure selection of the highest affinity phage antibodies; 3) What is the most efficient techniques for making mutant phage antibody libraries (random mutagenesis or site directed mutagenesis; 4) What region of the antibody molecule should be selected for mutagenesis to most efficiently increase antibody fragment affinity.

To answer these questions, we studied the human scFv C6.5, which binds the extracellular domain (ECD) of the tumor antigen ErbB-2 (32) with a $K_d$ of $1.6 \times 10^{-8}$M and $k_{off}$ of $6.3 \times 10^{-3} s^{-1}$ (Schier et al. (1995) *Immunotechnology,* 1: 63–71). Isolation and characterization of C6.5 is described briefly below and in detail in copending application U.S. Ser. No. 08/665,202).

Despite excellent tumor:normal tissue ratios in vivo, quantitative delivery of C6.5 was not adequate to cure tumors in animals using radioimmunotherapy (Schier et al. (1995) *Immunotechnology,* 1: 63–71). To improve the quantitative delivery of antibody to tumor, the affinity of C6.5 was increased. First, techniques were developed that allowed selection of phage antibodies on the basis of affinity, rather than differential growth in *E. coli* or host strain toxicity (Schier et al. (1996) *J. Mol. Biol.* 255: 28–43; Schier et al. (1996) *Gene* 169: 147–155; Schier et al. (1996) *Human antibodies and hybridomas* 7: 97–105). Next, we determined which locations in the scFv gene to mutate to achieve the greatest increments in affinity (Schier et al. (1996) *J. Mol. Biol.* 255: 28–43; Schier et al. (1996) *Gene*; Schier et al. (1996) *J. Mol. Biol.* 263: 551–567). Random mutagenesis did not yield as great an increment in affinity as site directed mutagenesis of the complementarity determining regions (CDRs) that contain the amino acids which contact antigen. Results from diversifying the CDRs indicated that: 1) the greatest increment in affinity was achieved by mutating the CDRs located in the center of the binding pocket ($V_L$ and $V_H$ CDR3); 2) half of the CDR residues have a structural role in the scFv and when mutated return as wild-type; and 3) these structural residues can be identified prior to library construction by modeling on a homologous atomic crystal structure. These observations led to development of a generic strategy for increasing antibody affinity where mutations are randomly introduced sequentially into $V_H$ and $V_L$ CDR3, with conservation of residues postulated to have a structural role by homology modeling (Schier et al. (1996) *J. Mol. Biol.* 263: 551–567). Using this approach, the affinity of C6.5 was increased 1200 fold to a Kd of $1.3 \times 10^{-11}$M (Id.).

Biodistribution studies revealed a close correlation between affinity and the percent injected dose of scFv/gram of tumor (%ID/g) at 24 hours (Adams et al. (1998) *Cancer Res.* 58: 485–490). The greatest degree of tumor retention was observed with $^{125}$I-C6ML3-9 (1.42%ID/g, $K_d$=1.0×10⁻⁹M). Significantly less tumor retention was achieved with $^{125}$I-C6.5 (0.80%ID/g, $K_d$=1.6×10⁻⁸) and C6G98A (0.19%ID/g, $K_d$=3.2×10⁻⁷M). The tumor:normal organ ratios also reflected the differences in affinity, e.g. tumor-:blood ratios of 17.2, 13.3, 3.5 and 2.6, and tumor to liver ratios of 26.2, 19.8, 4.0 and 3.1 for C6ML3-9, C6.5 and C6G98A respectively at 24 hours. Studies of the higher affinity scFv are pending. The results demonstrate our ability to increase antibody affinity to values not achievable from hybridoma technology and confirm the importance of affinity in tumor targeting Example 4

Preclinical Development of C6.5 Based Breast Cancer Therapies

Two approaches have been collaboratively pursued to develop C6.5 based breast cancer therapies. C6.5 based molecules are being engineered for radioimmunotherapy. To increase quantitative tumor delivery and retention of antibody fragment, dimeric scFv 'diabodies' were created by shortening the linker between the $V_H$ and $V_L$ domains from 15 to 5 amino acids. Consequently, pairing occurs between complementary domains of two different chains, creating a stable noncovalently bound dimer with two binding sites. In vitro, diabodies produced from the V-genes of C6.5 have a significantly higher apparent affinity and longer retention on the surface of SK-OV-3 cells compared to C6.5 scFv ($T_{1/2}$>5 hr vs. 5 min) (Adams et al. (1998) *Brit. J. Cancer.*). Biodistribution studies of C6.5 diabody revealed 6.5%ID/g tumor at 24 hours compared to only 1%ID/g for C6.5 scFv. When diabody retentions were examined over 72 hours and cumulative area under the curve (AUC) values determined, the resulting tumor:organ AUC ratios were greater than reported for other monovalent or divalent scFv molecules. The therapeutic potential of these molecules is being examined in radioimmunotherapy studies in nude mice. Since in vivo characterization of c6.5 based molecules was not formally one of the technical objectives, we are continuing to use the affinity mutants of C6.5 and C6.5 based diabodies to study the relationship between antibody affinity, size and valency and specific tumor targeting as part of NIH R01 1 CA65559-01A1.

In another collaboration C6.5 based molecules are being used to target doxorubicin containing stealth liposomes to ErbB2 expressing breast cancers (Kirpotin et al. (1997) Biochemistry. 36: 66–75). To facilitate chemical coupling of the scFv to liposomes, the C6.5 gene was subcloned into an E. coli expression vector resulting in addition of a free cysteine residue at the C-terminus of the scFv. Purified C6.5cys scFv was conjugated to liposomes and in vitro uptake determined using SKBR3 cells. Total uptake was 3.4 mmol phospholipid/$10^6$ cells at 6 hour, with 70% of the uptake internalized. The uptake is comparable to that achieved using the 4D5 anti-HER2 Fab' from Genentech. There was no uptake of unconjugated liposomes. The results indicate that C6.5 binds to a ErbB2 epitope that results in internalization at a rate comparable to the best internalizing antibody produced from hybridomas (4D5). In vivo therapy studies in scid mice indicated that C6.5 targeted liposomes caused a greater degree of tumor regression and a higher cure rate than untargeted liposomes or a combination of untargeted liposomes and systemic 4D5 antibody.

Conclusions

The experiments described herein establish that A large ($7.0 \times 10^9$ member) phage antibody library has been created which can provide panels of human antibodies to purified antigens with affinities comparable to the affinities of antibodies produced by murine immunization. The phage antibodies binding cell surface receptors can be can be internalized by cells and recovered in an infectious state from within the cell. Methodologies were developed which permit enrichment of internalizing phage antibodies over non-internalizing antibodies more than 100 fold. These methodologies were then applied to select new scFv antibodies that bind to internalizing receptors on SKBR-3 cells. Several of these antibodies bind to ErbB2, but are internalized more efficiently than C6.5 based scFv. Many more antibodies bind to unknown internalizing receptors. All of these scFv bind specifically to SKBR-3 cells or related tumor cell lines. The results indicate that this selection approach is a powerful approach to generate antibodies that can distinguish one cell type (malignant) from another (non-malignant). Moreover, we have demonstrated that it is not only possible to select for binding, but to select for function (internalization). In the near term, we will further characterize the antibodies isolated with respect to specificity, and in the case of ErbB2 binding scFv, affinity. In the longer term we will use these reagents to: 1) study the effect of affinity and valency on the rate of internalization; and 2) identify the antigens bound using immunoprecipitation. It is likely that the results will lead to the identification of novel internalizing tumor cell surface receptors which will be useful therapeutic targets. If this approach proves useful, we plan on applying it to primary tumor cells and DCIS. We also intend to evaluate 3TF5 (ErbB2 binding scFv which is internalized faster than C6.5) for liposome targeting. It is possible that it will be more effective than C6.5

In addition, the experiments demonstrate that methodologies for increasing antibody affinity in vitro to values not previously achieved in vivo. We have applied these methodologies to generate novel ErbB2 binding scFv.

Example 5

Selection of Internalizing Antibodies from Phase Libraries

In this example, we studied a human scFv (C6.5) that binds ErbB2 to determine the feasibility of directly selecting internalizing antibodies from phage libraries and to identify the most efficient display format. Using wild type C6.5 scFv displayed monovalently on a phagemid, we demonstrate that anti-ErbB2 phage antibodies can undergo receptor mediated endocytosis. Using affinity mutants and dimeric diabodies of C6.5 displayed as either single copies on a phagemid or multiple copies on phage, we define the role of affinity, valency, and display format on phage endocytosis and identify the factors that lead to the greatest enrichment for internalization. Phage displaying bivalent diabodies or multiple copies of scFv were more efficiently endocytosed than phage displaying monomeric scFv and recovery of infectious phage was increased by preincubation of cells with chloroquine. Measurement of phage recovery from within the cytosol as a function of applied phage titer indicates that it is possible to select for endocytosable antibodies, even at the low concentrations that would exist for a single phage antibody member in a library of A) Material and Methods 1) Cells The SKBR3 breast tumor cell line was obtained from ATCC and grown in RPMI media supplemented with 10% FCS (Hyclone) in 5% $CO_2$ at 37° C.

2) Antibodies and Antibody Phage Preparations

The C6.5 scFv phage vector was constructed by subcloning the C6.5 gene as a Sfi I/Not I fragment from scFv C6.5 pHEN1 (Schier et al. (1995) Immunotechnology 1: 63–71) into the phage vector fd/Sfi I/Not I (a gift of Andrew Griffiths, MRC Cambridge, UK). The C6.5 diabody phagemid vector was constructed by subcloning the C6.5 diabody gene (Adams et al. (1998) Brit. J Cancer. 77: 1405–1412, 1998) as a NcoI/NotI fragment into pHEN1 (Hoogenboom et al. (1991) Nucleic Acids Res. 19: 4133–4137). The anti-botulinum scFv phagemid (clone 3D12) (Amersdorfer et al. (1997) Infection and Immunity. 65: 3743–3752) C6.5 scFv phagemid (Schier et al (1995) Immunotechnology 1: 63–71) and scFv C6ML3-9 scFv phagemid (Schier et al. (1996) J. Mol. Biol. 263: 551–567) in pHEN1 have been previously described. Phage were prepared (Sambrook et al. (1990). Molecular cloning-a laboratory manual, New York: Cold Spring Harbor Laboratory) from the appropriate vectors and titered on E. coli TG1 as previously described (Marks et al. (1991) J. Mol. Biol. 222: 581–597) using ampicillin (100 µg/ml) resistance for titration of constructs in pHEN1 and tetracyline (50 µg/ml) for titration of constructs in fd. Soluble C6.5 scFv, C6.5 diabody and anti-botulinum scFv were expressed from the vector pUC 119mycHis (Schier et al. (1995) Immunotechnology 1: 63–71) and purified by immobilized metal affinity chromatography as described elsewhere (Id.)).

3) Detection of Internalized Native Antibody Fragments and Phage Antibodies

SKBR3 cells were grown on coverslips in 6-well culture plates (Falcon) to 50% of confluency. Culture medium was renewed 2 hours prior to the addition of $5.10^{11}$ cfu/ml of phage preparation (the phage preparation representing a maximum of 1/10 of the culture medium volume) or 20 µg/ml of purified scFv or diabody in phosphate buffered saline, pH 7.4 (PBS). After 2 hours of incubation at 37° C. the wells were quickly washed 6 times with ice cold PBS and 3 times for 10 minutes each with 4 mL of stripping buffer (50 mM glycine pH 2.8, 0.5 M NaCl, 2M urea, 2% polyvinylpyrrolidone) at RT. After 2 additional PBS washes, the cells were fixed in 4% paraformaldehyde (10 minutes at RT), washed with PBS, permeabilized with acetone at −200° C. (30 seconds) and washed again with PBS. The coverslips were saturated with PBS—1% BSA (20 min. at RT). Phage particles were detected with biotinylated anti-M13 immunoglobulins (5 Prime-3 Prime, Inc, diluted 300 times)(45 min. at RT) and Texas red-conjugated streptavidin (Amersham, diluted 300 times)(20 min. a RT). Soluble scFv and diabodies containing a C-terminal myc peptide tag were detected with the mouse mAb 9E10 (Santa Cruz Biotech, diluted 100 times)(45 min. at RT), anti-mouse biotinylated immunoglobulins (Amersham, diluted 100 times) and Texas red-conjugated streptavidin. Opt cal confocal sections were taken using a BIO-RAD® MRC 1024 scanning laser confocal microscope. Alternatively, slides were analyzed with a Zeiss Axioskop UV fluorescent microscope.

4) Recovery and Titration of Cell Surface Bound or Internalized Phage

Subconfluent SKBR3 cells were grown in 6-well plates. Culture medium was renewed 2 hours prior to the experiment. Cells were incubated for varying times with different concentrations of phage preparation at 37° C. Following PBS and stripping buffer washes, performed exactly as described above for detection of internalized native antibody fragments and phage antibodies, the cells were washed again twice with PBS and lysed with 1 mL of 100 mM triethylamine (TEA). The stripping buffer washes and the TEA lysate were neutralized with ½ volume of Tris-HCl 1M, pH 7.4. For some experiments, cells were trypsinized after the three stripping buffer washes, collected in a 15 ml Falcon tube, washed twice with PBS and then lysed with TEA. In experiments performed in the presence of chloroquine, SKBR3 cells were preincubated for two hours in the presence of complete medium containing 50 µM chloroquine prior to the addition of phage. Corresponding control samples in the absence of chloroquine were prepared at the same time. For all experiments, phage were titered on $E.\ coli$ TG1 as described above.

B) Results

1) The Model System Utilized to Study Phase Antibody Internalization

The human anti-ErbB2 scFv C6.5 was obtained by selecting a human scFv phage antibody library on recombinant ErbB2 extracellular domain (13). C6.5 scFv binds ErbB2 with a $K_d=1.6\times10^{-8}$M and is a stable monomeric scFv in solution with no tendency to spontaneously dimerize or aggregate (Schier et al. (1995) Immunotechnology 1: 63–71). To determine the impact of affinity on internalization, we studied a scFv (C6ML3-9) which differs from C6.5 by 3 amino acids (Schier et al. (1996) J. Mol. Biol. 263: 551–567). C6ML3-9 scFv is also a stable monomer in solution and binds the same epitope as C6.5 scFv but with a 16 fold lower $K_d$ ($1.0\times10^{-9}$M) (Schier et al. (1996) J. Mol. Biol. 263: 551–567; Adams et al. (1998) Cancer Res. 58: 485–490). Since receptor homodimerization appears to typically be requisite for antibody internalization we also studied the dimeric C6.5 diabody (Adams et al. (1998) Brit. J. Cancer. 77: 1405–1412, 1998). Diabodies are scFv dimers where each chain consists of heavy ($V_H$) and light ($V_L$) chain variable domains connected using a peptide linker which is too short to permit pairing between domains on the same chain. Consequently, pairing occurs between complementary domains of two different chains, creating a stable noncovalent dimer with two binding sites (Holliger et al. (1993) Proc. Natl. Acad. Sci. 90: 6444–6448). The C6.5 diabody was constructed by shortening the peptide linker between the Ig $V_H$ and $V_L$ domains from 15 to 5 amino acids and binds ErbB2 on SKBR3 cells bivalently with a $K_d$ approximately 40 fold lower than C6.5 ($4.0\times10^{-10}$M) (Adams et al. (1998) Brit. J Cancer. 77: 1405–1412, 1998).

Native C6.5 scFv and C6.5 diabody was expressed and purified from $E.\ coli$ and analyzed for endocytosis into ErbB2 expressing SKBR3 breast tumor cells by immunofluorescent confocal microscopy. As expected, monomeric C6.5 scFv is not significantly internalized whereas the dimeric C6.5 diabody can be detected in the cytoplasm of all cells visualized.

Figure 2B:
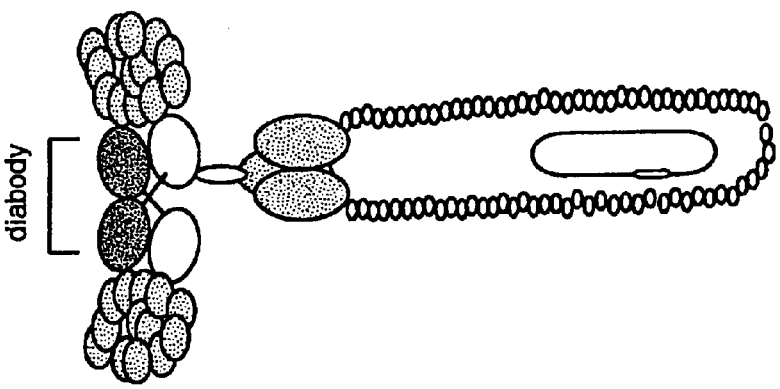
Figure 2C:
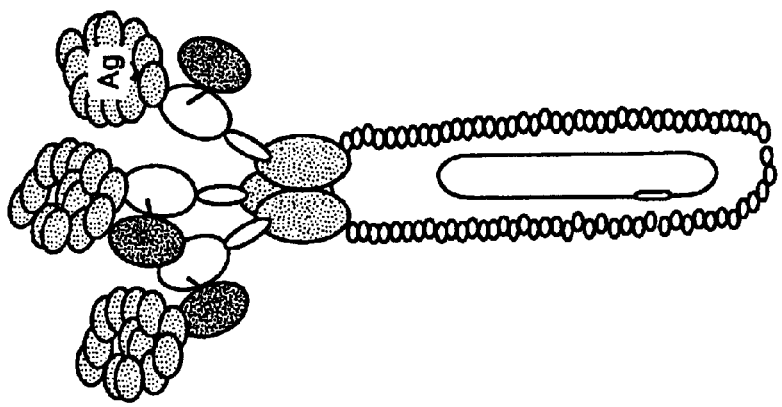

For subsequent experiments, the C6.5 and C6ML3-9 scFv and C6.5 diabody genes were subcloned for expression as pIII fusions in the phagemid pHEN-1 (Hoogenboom et al. (1991) Nucleic Acids Res. 19: 4133–4137). This should yield phagemid predominantly expressing a single scFv or diabody-pIII fusion after rescue with helper phage (Marks et al. (1992) J. Biol. Chem. 267: 16007–16010) (FIGS. 2A and 2B). Diabody phagemid display a bivalent antibody fragment resulting from intermolecular pairing of one scFv-pIII fusion molecule and one native scFv molecule (FIG. 2B). The C6.5 scFv gene was also subcloned into the phage vector fd-Sfi/Not. This results in phage with 3 to 5 copies each of scFv-pIII fusion protein (FIG. 2C). The human breast cancer cell line SKBR3 was used as a target cell line for endocytosis. Its surface ErbB2 density is approximately $1.0\times10^6$ per cell (Hynes et al. (1989) J. Cell. Biochem 39: 167–173).

2) C6.5 Phagemids are Endocytosed by Human Cells

C6.5 scFv phagemids were incubated for 2 hours with SKBR3 cells grown on coverslips at 37° C. to allow active internalization. Cells were extensively washed with PBS to remove non specific binding and washed an additional three times with high salt and low pH (stripping) buffer to remove phage specifically bound to cell surface receptors. Internalized phagemid were detected with a biotinylated M13 antiserum recognizing the major coat phage protein pVIII. An anti-botulinum toxin phagemid was used as a negative control. Staining was analyzed by using immunofluorescent microscopy. Approximately 1% of the cells incubated with C6.5 scFv phagemid showed a strong intracellular staining consistent with endosomal localization while no staining was observed for anti-botulinum phagemid. Furthermore, no staining was seen if the incubation was performed for 2 hours at 4° C. instead of 37° C. (data not shown). Staining performed after the PBS washes but before washing with stripping buffer showed membrane staining of all the cells, indicating that multiple washes with stripping buffer is necessary to remove surface bound phagemids. The results also indicate that only a fraction of the cell bound phage are endocytosed.

3) Increased Affinity and Bivalency Lead to Increased Phase Endocytosis

We compared the internalization of C6.5 scFv, C6ML3-9 scFv and C6.5 diabody phagemid and C6.5 scFv phage using immunofluorescence. Both C6ML3-9 scFv and C6.5 diabody phagemid as well as C6.5 scFv phage yielded increased intensity of immunofluorescence observed at the cell surface compared to C6.5 scFv phagemid. For C6ML3-9 scFv phagemid, approximately 10% of the cells showed intracellular fluorescence after 2 hours of incubation. This value increased to approximately 30% of cells for the dimeric C6.5 diabody phagemid and 100% of cells for multivalent C6.5 scFv phage.

3) Infectious Phage can be Recovered from within the Cell and Their Titre Correlates with the Level of Uptake Observed Using Immunofluorescence To determine if infectious phage antibody particles could be recovered from within the cell, we incubated approximately $5.0 \times 10^5$ SKBR-3 cells for 2 hours at 37° C. with $3.0 \times 10^{11}$ cfu of the different phagemid or phage. Six PBS washes were used to remove non-specifically bound phage and specifically bound phage were removed from the cell surface by three consecutive washes with stripping buffer (washes I, II and III respectively, Table 6). The cells were then lysed with 1 mL of a 100 mM triethylamine solution (TEA) (representing the intracellular phage). The three stripping washes and the cell lysate were neutralized and their phage titer was determined by infection of E. coli TG1. The titers of phage recovery are reported in Table 6.

TABLE 6

Titration of membrane bound and intracellular phage. $3.0 \times 10^{11}$ cfu of monovalent C6.5 scFv phagemid, 16 fold higher affinity monovalent C6ML3-9 scFv phagemid, bivalent C6.5 diabody phagemid or multivalent C6.5 fd phage were incubated with sub confluent SKBR3 cells for 2 hours at 37° C.. Cells were washed 6 times with PBS, 3 times with stripping buffer and then lysed to recover intracellular phage. The various fractions were neutralized and the phage titered. The total number of cfu of each fraction is reported. Non specific anti-botulinum phagemid were used to determine non specific recovery.

| Phage Antibody | Cell Surface Phage Titer ($\times 10^{-5}$) | | | Intracellular Phage Titer ($\times 10^{-5}$) |
| --- | --- | --- | --- | --- |
| | 1st Wash | 2nd Wash | 3rd Wash | |
| Anti-botulinum phagemid | 280 | 36 | 2.8 | 15 |
| C6.5 scFv phagemid | 600 | 96 | 7.6 | 52 |
| C6ML3-9 scFv phagemid | 2500 | 140 | 32 | 270 |
| C6.5 diabody phagemid | 1800 | 120 | 13 | 450 |
| C6.5 scFv phage | 2300 | 620 | 56 | 2200 |

Considerable background binding was observed in the first stripping wash for the anti-botulinum phage even after 6 PBS washes ($2.8 \times 10^7$ cfu, Table 6). This value likely represents phage non-specifically bound to the cell surface as well as phage trapped in the extracellular matrix. The amount of surface bound phage increased only 2.1 fold above this background for C6.5 scFv phagemid (Tables 6 and 7). With increasing affinity and avidity of the displayed C6.5 antibody fragment, the titer of cell surface bound phagemid or phage increased (Table 6). The titer of phage in the consecutive stripping washes decreased approximately 10 fold with each wash. These additional stripping washes led to a minor increase in the titer of specific phage eluted compared to the background binding of the anti-botulinum phage (2.7 fold for C6.5 scFv phagemid to 20 fold for C6.5 scFv phage, Table 7). The only exception was the titer of the C6.5 diabody phagemid, where the ratio actually decreased from 6.4 fold to 4.6 fold. This is likely due to the fact that in the diabody the $V_H$ and $V_L$ domains that comprise a single binding site are not covalently attached to each other via the peptide linker. This increases the likelihood that a stringent eluent (like glycine) could dissociate $V_H$ from $V_L$ and abrogate binding to antigen.

TABLE 7

Specific enrichment of anti-ErbB2 phage compared to anti-botulinum phage. *The titers of anti-ErbB2 phage are divided by the titers of the anti-botulinum phage (Table 6) to derive an enrichment ratio for specific vs nonspecific binding or internalization **The titer of intracellular phage is divided by the titer of cell surface bound phage (Table 6) to derive the ratio of internalized phage vs surface bound phage.

| | Anti-ErbB2/Anti-Botulinum Phage Titer Ratio* | | | Intracellular/ |
| --- | --- | --- | --- | --- |
| Phage Antibody | Cell surface (1st Wash) | Cell surface (3rd Wash) | Intracellular | Cell Surface Phage Ratio** |
| C6.5 scFv phagemid | 2.14 | 2.7 | 3.5 | 6.8 |
| C6ML3-9 scFv phagemid | 8.9 | 11.4 | 18 | 8.4 |
| C6.5 diabody phagemid | 6.4 | 4.6 | 30 | 35 |
| C6.5 scFv phage | 8.2 | 20 | 146 | 39 |

Three stripping washes were required to ensure that the titer of phage recovered after cell lysis was greater than the titer in the last stripping wash (Table 6). We presumed that after three stripping washes, the majority of the phage eluted represented infectious particles from within the cell rather than from the cell surface. In fact, since the cell lysate titer observed with non-specific anti-botulinum phage was considerable ($1.5 \times 10^6$) and greater than observed in the last stripping wash, it is likely that many phage remain trapped within the extracellular matrix and relatively inaccessible to the stripping buffer washes. Some anti-botulinum phage might also be non-specifically endocytosed by cells, but this is likely to be a small amount given the immunofluorescence results. The titer of phage in the TEA fraction increased with increasing affinity and avidity of C6.5, with the highest titers observed for the dimeric C6.5 diabody phagemid and the multivalent C6.5 scFv phage (Table 6). The values represent a 30 fold (C6.5 diabody phagemid) and 146 fold (C6.5 scFv phage) increase in titer compared to the anti-botulinum phage (Table 6). We have presumed that the increase in the phage titer in the cell lysate compared to the last stripping wash is due to endocytosed phage. In fact, some of these phage could have come from the cell surface or intracellular matrix. While this could be true for a fraction of the phage from the cell lysate, the immunofluorescence results indicate that at least some of the phage are endocytosed. One indicator of the relative fraction of endocytosed phage for the different C6.5 molecules is to compare the amount of phage remaining on the cell surface prior to cell lysis (last stripping wash) with the amount recovered after cell lysis. This ratio shows only a minor increase for monovalent C6.5 scFv or C6ML3-9 scFv phagemid (6.8 and 8.4 fold respectively) compared to anti-botulinum phagemid (5.4) (Table 7). In contrast the ratios for dimeric C6.5 diabody phagemid and multivalent C6.5 scFv phage increase to a greater extent (35 and 39 respectively) compared to anti-botulinum phagemid.

4) Increasing the Enrichment Ratios of Specifically Endocytosed Phage

The results above indicate that phage antibodies can undergo receptor mediated endocytosis and remain infectious in a cell lysate. Selection of internalized phages from a phage library requires the optimization of the method to increase enrichment of specifically internalized phages over non-internalized phage. Two parameters can be improved: (1) reduction of the recovery of non-specific or non-internalized phage and (2) preservation of the infectivity of internalized phage. To examine these parameters, we studied wild-type C6.5 scFv phagemid. We chose this molecule because it was clearly endocytosed based on confocal microscopy, yet was the molecule undergoing the least degree of specific endocytosis. C6.5 scFv phagemid also represents the most commonly utilized format for display of non-immune phage antibody libraries (single copy pIII in a phagemid vector) and has an affinity (16 nM) more typical of Kd's of scFv from such libraries than the affinity matured C6ML3-9 scFv (Sheets et al. (1998) *Proc. Natl. Acad. Sci. USA* 95: 6157–6162; Vaughan et al. (1996) *Nature Biotech.* 14: 309–314).

a) Reducing the Background of Non-Internalized Phage

To reduce the background of non-specific phage recovery, we studied the effect of trypsinizing the cells prior to TEA lysis. This should remove phage trapped in the extracellular matrix. Trypsinization also dissociates the cells from the cell culture flask, permitting transfer to a new vessel and elimination of any phage bound to the cell culture flask. For these experiments, C6.5 scFv phagemid ($5.0 \times 10^8$ ampicillin resistant cfu) were mixed with a 1000 fold excess of wild type fd phage ($5.0 \times 10^{11}$ tetracylcine resistant cfu). After incubation of phagemid with SKBR-3 cells for 2 hours at 37° C., cells were washed with PBS and three times with stripping buffer. Cells were then directly lysed with TEA or treated with trypsin, washed twice with PBS and then lysed with TEA. Phagemid in the first stripping wash and the cell lysate were titered by infection of *E. coli* TG1 and plated on ampicillin and tetracycline plates. The titer of fd phage and C6.5 scFv phagemid recovered from the cell surface was comparable for the two experimental groups (FIG. 3). The ratio of fd phage/C6.5 scFv phagemid in the cell surface fractions ($^{160}/_1$ and $^{250}/_1$) yields a 4 to 6 fold enrichment achieved by specific cell surface binding from the initial 1000 fold ratio. Without trypsinization, the ratio of fd phage/C6.5 scFv phagemid in the cell lysate increases only 6.1 fold; in contrast, the ratio increases 209 fold with trypsinization (FIG. 3). This results from a 60 fold reduction in non-specific binding with only a minor reduction in the amount of specific phage recovery (FIG. 3).

b) Improving the Recovery of Infectious Internalized Phage

To increase the recovery of infectious internalized phage, we studied whether prevention of lysosomal acidification through the use of chloroquine would protect endocytosed phages from endosomal degradation (Barry et al. (1996) *Nat. Med.* 2: 299–305). SKBR3 cells were incubated with chloroquine and either C6.5 scFv phagemid or anti-botulinum phagemid. Cell lysates were titered at various time points to determine the number of intracellular phagemid. C6.5 scFv phagemid were present at the 20 minute time point and the amount of phagemid was comparable with or without the addition of chloroquine. At later time points, approximately twice as much infectious phagemid was recovered with the use of chloroquine. In contrast, much lower amounts of anti-botulinum phage were present and chloroquine had no effect on the titer, suggesting that the phagemid result from non-specific surface binding rather than non-specific endocytosis into endosomes. Overall, the results indicate that prevention of lysosomal acidification increases the amount of infectious phage recovered for incubations longer than 20 minutes.

5) Recovery of Internalized Phage at low Phage Concentrations

Only very large phage antibody libraries containing more than $5.0 \times 10^9$ members are capable of generating panels of high affinity antibodies to all antigens (10, 23, 24). Since phage can only be concentrated to approximately $10^{13}$ cfu/ml, a typical phage preparation from a large library will only contain $10^4$ copies of each member. Thus selection of libraries for endocytosis could only work if phage can be recovered when applied to cells at titers as low as $10^4$. We therefore determined the recovery of infectious phage from within SKBR3 cells as a function of the phage titer applied. SKBR3 cells were incubated with C6.5 scFv, C6ML3-9 scFv or C6.5 diabody phagemids or C6.5 scFv phage for 2 hours at 37° C. Cells were washed three times with stripping buffer, trypsinized and washed twice with PBS. Cells were lysed and intracellular phage titered on *E. coli* TG1. Phage recovery increased with increasing phage titer for all phage studied (FIG. 5). For monovalently displayed antibodies, phagemid could not be recovered from within the cell at input titers less than $3.0 \times 10^5$ (C6.5 scFv) to $3.0 \times 10^6$ (C6ML3-9 scFv) This threshold decreased for bivalent and multivalent display ($3.0 \times 10^4$ for C6.5 diabody phagemid and C6.5 scFv phage).

C) Discussion

We demonstrate for the first time that phage displaying an anti-receptor antibody can be specifically endocytosed by receptor expressing cells and can be recovered from the cytosol in infectious form. The results demonstrate the feasibility of directly selecting internalizing antibodies from large non-immune phage libraries and identify the factors that will lead to successful selections. Phage displaying anti-ErbB2 antibody fragments are specifically endocytosed by ErbB2 expressing SKBR3 cells, can be visualized within the cytosol and can be recovered in an infectious form from within the cell. When monovalent scFv antibody fragments were displayed monovalently in a phagemid system, recovery of internalized phage was only 3.5 to 18 fold above background. Display of bivalent diabody or multivalent display of scFv in a phage vector increased recovery of internalized phage to 30 to 146 fold above background. This result is consistent with our studies of native monomeric C6.5 scFv and dimeric C6.5 diabody as well as studies of other monoclonal anti-ErbB2 antibodies where dimeric IgG but not monomeric Fab dimerize and activate the receptor and undergo endocytosis (Yarden (1990) *Proc. Natl. Acad. Sci. USA* 87: 2569–2573; Hurwitz et al. (1995) *Proc. Natl. Acad. Sci. USA* 92: 3353–3357). In fact it is likely that endocytosis of C6.5 and C6ML3-9 scFv phagemids reflect the small percentage of phage displaying two or more scFv (Marks et al. (1992) *J. Biol. Chem.* 267: 16007–16010). The importance of valency in mediating either high avidity binding or receptor crosslinking and subsequent endocytosis is confirmed by the only other report demonstrating specific phage endocytosis. Phage displaying approximately 300 copies of a high affinity Arg-Gly-Asp integrin binding peptide on pVIII were efficiently endocytosed by mammalian cells (Hart et al. (1994) *J. Biol. Chem.* 269: 12468–12474). Recovery of phage after endocytosis also increases the specificity of cell selections compared to recovery of phage from the cell surface. Thus enrichment ratios for specific vs non-specific surface binding range from 2 to 20 fold. These values are comparable to the approximately 10 fold enrichment reported by others for a single round of cell surface selection (Pereira et al. (1997) *J. Immunol. Meth.* 203: 11–24; Watters et al. (1997) *Immunotechnology* 3: 21–29). In contrast our enrichment ratios for specific vs non-specific endocytosis range from 3.5 to 146 fold.

Based on these results, selection of internalizing antibodies from phage antibody libraries would be most successful with either homodimeric diabodies in a phagemid vector or multivalent scFv using a phage vector. While no such libraries have been published, there are no technical barriers preventing their construction. Multivalent libraries would present the antibody fragment in the form most likely to crosslink receptor and undergo endocytosis. Antibodies from such libraries would need to be bivalent to mediate endocytosis. Alternatively, monomeric receptor ligands can activate receptors and undergo endocytosis, either by causing a conformational change in the receptor favoring the dimeric form or by simultaneously binding two receptors. Monomeric scFv that bound receptor in a similar manner could also be endocytosed. Thus selection of libraries of monovalent scFv in a phagemid vector could result in the selection of ligand mimetics that activate receptors and are endocytosed as monomers. Such scFv could be especially useful for the construction of fusion molecules for the delivery of drugs, toxins or DNA into the cytoplasm. Since antibodies which mediate receptor internalization can cause receptor down regulation and growth inhibition (Hurwitz et al. (1995) *Proc. Natl. Acad. Sci. USA* 92: 3353–3357; Hudziak et al. (1989) *Mol. Cell. Biol.* 9: 1165–1172; Stancovski et al. (1991) *Proc. Natl. Acad. Sci. USA* 88: 8691–8698; Lewis et al. (1993) *Cancer Immunol. Immunother.* 37: 255–263), selection for endocytosable antibodies may also identify antibodies which directly inhibit or modulate cell growth.

Example

Transfection of Cells

The F5 scFv gene was removed from pHEN1-F5 by digestion of phagemid DNA with the restriction enzymes SfiI and NotI. A phage vector based on FdDOG1 (See prior Ref.), but modified to insert an SfiI site into the gene III leader sequence, was digested with SfiI and NotI and the digested F5 gene ligated into digested phage Fd vector DNA. Recombinant transformant were identified. *E. coli* containing the F5 recombinant phage were grown in culture to produce F5-Fd phage (see Maniatis for phage preparation). F5 phages were then used to infect *E. coli* harboring a phagemid which contains a mammalian promoter (CMV) followed by either the gene for ꓱ-galactosidase (pcDNA3.1/HisB/LacZ, In Vitrogen) or the gene for the enhanced green fluorescent protein (pN2EGFP, Clonetch plasmid) and a eucaryotic polyadenylation sequence. Bacteria were grown overnight in the presence of tetracycline 15 ug/mL and either ampicillin 100 ug/mL (pcDNA3.1/HisB/LacZ containing bacteria) or Kanamycine 30 ug/mL (pN2EGFP containing bacteria). The phage prepared from the supernatant a mixture of F5-Fd coat contains either the reporter gene (about 50% of the phages) in a single strand format or the F5-Fd phage genome (about 50% of the phages). Incubation of ErbB2 positive cells 5.105 SKBR3 with $10^7$ pfu the phage mix (Filtered twice through a 0.45 nm filter to sterility) allowed expression of the reporter gene in 1% of the cells. Cells incubated with an 10 time fold more negative control phage, i.e. reporter gene packaging in wild type Fd, showed no expression of the reporter genes. In an experiment where a mixed population of ErbB2 high (SKBR3) and ErbB2 low cells (MCF7) (Lewis et al. (1993) *Cancer Immunol Immunother* 37: 255–263) were incubated with the F5-Fd-EGFP phages for two days, we obtained the expression of the reporter gene only in erbB2 positive cells, cells being differentiated by their ErbB2 level by FACS.

Example 6

Targeted Gene Delivery to Mammalian Cells by Filamentous Bacteriophage

In this example we show that prokaryotic viruses can be re-engineered to infect eukaryotic cells resulting in expression of a portion of the bacteriophage genome. Phage capable of binding mammalian cells expressing the growth factor receptor ErbB2 and undergoing receptor mediated endocytosis were isolated by selection of a phage antibody library on breast tumor cells and recovery of infectious phage from within the cell. As determined by Immunofluorescence, F5 phage were efficiently endocytosed into 100% of ErbB2 expressing SKBR3 cells. To achieve expression of a portion of the phage genome, F5 phage were engineered to package the green fluorescent protein (GFP) reporter gene driven by the CMV promoter. These phage when applied to cells underwent ErbB2 mediated endocytosis leading to GFP expression. GFP expression occurred only in cells overexpressing ErbB2, was dose dependent reaching 4% of cells after 60 hours and was detected with phage titers as low as $2.0 \times 10^7$ cfu/ml (500 phage/cell). The results demonstrate that bacterial viruses displaying the appropriate antibody can bind to mammalian receptors and utilize the endocytic pathway to infect eukarotic cells resulting in viral gene expression. This represents a novel method to discover targeting molecules capable of delivering a gene intracellularly into the correct trafficking pathway for gene expression by directly screening phage antibodies. This should significantly facilitate the identification of appropriate targets and targeting molecules for gene therapy or other applications where delivery into the cytosol is required. This approach can also be adapted to directly select, rather than screen, phage antibodies for targeted gene expression. The results also demonstrate the potential of phage antibodies as an in vitro or in vivo targeted gene delivery vehicle.

A) Introduction

Widespread application of gene therapy requires the ability to target a therapeutic gene to the appropriate cell or tissue type with high efficiency (Michael and Curiel (1994) *Gene Ther.* 1: 223–232). Targeting of retroviral vectors has been reported by inserting receptor ligands or single chain Fv (scFv) antibody fragments into the viral envelope protein (Kasahara et al. (1994) *Science* 266: 1373–1376). Targeting of adenoviral vectors has been achieved by use of 'adapter' fusion molecules consisting of an antibody fragment which binds the adenoviral knob and a cell targeting molecule such as a receptor ligand or antibody (Douglas et al. (1996) *Nat. Biotechnol.* 14: 1574–1578; Watkins et al 1997) *Gene Ther.* 4(10): 1004–1012). Targeting of non-viral vectors using cell surface receptor ligands or antibodies has also been reported (Fominaya and Wels (1996) *J. Biol. Chem.* 271(18): 10560–10568; Michael and Curiel (1994) *Gene Ther.* 1: 223–232). All of these approaches depend on the use of targeting molecules which bind a cell surface receptor resulting in internalization of the gene delivery vehicle with subsequent delivery of the DNA to the nucleus. Identification of appropriate targeting molecules has largely been performed by individually screening receptor ligands or antibodies. In the case of scFv antibody fragments this typically requires construction of the scFv from the V-genes of a hybridoma, construction of the targeted gene delivery vehicle, and in vitro evaluation of targeting ability.

More recently, it has proven possible to directly select peptides and antibody fragments binding cell surface receptors from filamentous phage libraries (Andersen et al. (1996) *Proc. Natl. Acad. Sci. USA* 93(5): 1820–1824; Barry et al. (1996) *Nat. Med.* 2: 299–305; Cai and Garen (1995) *Proc. Natl. Acad. Sci. USA* 92(24): 6537–6541; de Kruif et al. (1995) *Proc. Natl. Acad. Sci. USA* 92(6): 3938–3942; Marks et al. (1993) *Bio/Technology* 11(10): 1145–1149). This has led to a marked increase in the number of potential targeting molecules. The ability of bacteriophage to undergo receptor mediated endocytosis (Barry et al. (1996) *Nat. Med.* 2: 299–305; Hart et al. (1994) *J. Biol. Chem.* 269(17): 12468–12474) indicates that phage libraries can be selected not only for cell binding but also for internalization into mammalian cells. If the phage single stranded phage genome can be transcribed and translated, then it should prove possible to screen or select for phage which bind receptors in a manner which leads to endocytosis and delivery of the phage genome into the correct trafficking pathway leading to expression. It has been previously shown that phage can enter mammalian cells after chemical alteration of the cell membrane leading to reporter gene expression (Okayama and Berg (1985) *Mol. Cell. Biol.* 5(5): 1136–1142; Yokoyama-Kobayashi and Kato (1993) *Biochem. Biophys. Res. Commun.* 193(2): 935–939). More recently, Larocca et al. showed that indirect bacteriophage mediated gene delivery could occur by targeting biotinylated phage via streptavidin and biotinylated fibroblast growth factor (FGF) to mammalian cells expressing FGF receptor (Larocca et al. (1998) *Hum. Gene Ther.* 9: 2393–2399).

In this report, we show that filamentous phage displaying the anti-ErbB2 scFv F5 as a genetic fusion with the phage minor coat protein pIII can directly infect mammalian cells expressing ErbB2 leading to expression of a reporter gene contained in the phage genome. This offers a new way to discover targeting molecules for intracellular drug delivery or gene therapy by directly screening phage antibodies to identify those capable of undergoing endocytosis and delivering a gene intracellularly into the correct trafficking pathway for gene expression. This should significantly facilitate the identification of appropriate targets and targeting molecules for gene therapy or other applications where delivery into the cytosol is required. We also discuss how this approach might be used to directly select phage antibodies for targeted gene expression. Finally, we discuss the potential for use of phage antibodies themselves for in vitro or in vivo targeted gene delivery vectors.

B) Materials and Methods

1) Anti-ErbB2 F5 scFv

An anti-ErbB2 scFv (F5) in the vector pHEN-1 (Hoogenboom et al. (1991) *Nucleic Acids Res.* 19(15): 4133–4137) (pHEN-F5) was obtained by selecting a non-immune phage antibody library (Sheets et al. (1998) *Proc. Natl. Acad. Sci. USA* 95(11): 6157–6162) on ErbB2 expressing SKBR3 cells followed by screening for binding on recombinant ErbB2 extracellular domain (ECD). The native F5 scFv binds ErbB2 ECD with a $K_d$=1.6×10$^{-7}$M as determined by surface plasmon resonance in a BIAcore as previously described (Schier et al. (1996) *J. Mol. Biol* 255(1): 28–43).

2) Phage and Phagemid Vectors pcDNA3-GFP (6.1 Kbp) was obtained by subcloning the Hind III/Not I fragment of pN2EGFP (4.7 Kbp) (Clontech) into the pcDNA3-HisB/LacZ (Invitrogen) Hind III/Not I backbone. A fd-F5-phage vector was constructed by subcloning the Sfi I/Not I scFv-F5 insert from pHEN-1 into the Sfi I/Not I sites of fd-Sfi/Not (constructed from fd-tet-DOG (Clackson et al. (1991) *Nature* 352(6336): 624–628) by changing the ApaL1 cloning site in the gene III leader to SfiI. The pHEN-F5-GFP phagemid vector (6.8 Kbp) was obtained by subcloning the 1.6 Kbp pN2EGFP blunted Ase I/Afl II fragment into the blunted EcoR I site of pHEN-F5. The orientation of the insert was analyzed by Not I restriction digest.

3) Cell Line Culture and Transfection

SKBR3 and MCF7 were grown in RPMI complemented with 10% fetal bovine serium (FBS) (Hyclone) 50% confluent SKBR3 cells grown in 6-well plates were transfected with 1 µg of DNA per well using LIPOFECTAMINE® (GIBCO BRL) as recommended by the manufacturer. pN$_2$EGFP dsDNA was prepared by alkaline lysis using the Maxiprep Qiagen Kit (Qiagen Inc.). ssDNA was extracted from 500 µl of phagemid preparation (see below) by 2 phenol extractions followed by ethanol precipitation. DNA was quantified by spectophotometry with 1.0 $A_{260}$ nm equal to 40 µg/ml for ssDNA or 50 µg/ml for dsDNA. For GFP detection, cells were detached using a trypsin-EDTA mix (GIBCO BRL) and analyzed on a FACScan (Becton Dickinson).

4) Phagemid and Phase Preparation pHEN-F5, pHEN-F5-GFP, pcDNA3-GFP or pN2EGFP phagemids were prepared from *E. coli* TG1 by superinfection with VCS-M13 helper phage (Stratagene) as previously described (Marks et al. (1991) *J. Mol. Biol.* 222(3): 581–597). Fd-F5-phage were prepared from *E. coli* TG1 as previously described (McCafferty et al. (1990) *Nature* 348 (6301): 552–554). F5-GFP-phage and F5-LacZ-phage were prepared by superinfection of *E coli* TG1 containing pcDNA3-GFP with fd-F5-phage. Virus particles were purified from the culture supernatant by 2 polyethylene glycol precipitations (Sambrook et al. (1990). *Molecular cloning—a laboratory manual*, Cold Spring Harbor Laboratory, New York) resuspended in phosphate buffered saline, pH 7.4 (PBS), filtered through a 0.45 µm filter and stored at 4° C. Alternatively, the preparations were submitted to an additional CsC1 ultracentrifugation step (Smith and Scott (1993) *Meth. EnzymoL* 217: 228–257). The ratio of packaged helper phage DNA versus phagemid DNA was determined by titering (Sambrook et al., supra.) the phage for ampicillin and kanamycin resistance (for helper phage rescued pHEN-F5) or ampicillin and tetracycline resistance (for fd-F5 phage rescued pcDNA3-GFP).

5) Phage FACS

Cells were trypsinized, washed with PBS containing 1% FBS (FACS buffer) and resuspended at 10 cells/ml in the same buffer. The staining procedure was performed on ice with reagents diluted in FACS buffer. One hundred µl aliquots of cells were distributed in conical-96-well plate (Nunc), centrifuged at 300 g and the cell pellets resuspended in 100 µl of serial dilutions of phage or phagemid preparation and incubated for 1 hr. Cells were centrifuged and washed twice, the cell pellets resuspended in 100 µl of anti-M13 antibody (5 Prime, 3 Prime Inc.) (diluted 1/400) and incubated for 45 min. Cells were washed as above, resuspended in 100 µl of streptavidin-Phycoerythrin (Jackson Inc.) (diluted 1/400) and incubated for 20 min. After a final wash, the cells were analyzed by FACS.

6) Immunofluorescence

Cells were grown on coverslips to 50% confluency in 6 well-plates. Phage preparation (less than 10% of the culture medium) was added and the cells were incubated for 16 hours. The coverslips were washed 6 times with PBS, 3 times for 10 min with Glycine buffer (50 mM glycine, pH 2.8, NaCl 500 mM), neutralized with PBS and fixed with PBS-4% paraformaldehyde for 5 min at room temperature. Cells were permeabilized with cold acetone for 30 sec, saturated with PBS-1% BSA and incubated with anti-M13 antibody (d:1/300 in the saturation solution) followed by streptavidin-Texas Red (Amersham) (d: 1/300 in the saturation solution). Coverslips were analyzed with an Axioskop fluorescent microscope (Zeiss).

7) Bacteriophage Mediated Cell Infection

CsCl phage preparations were diluted at least 10 fold in cell culture medium, filtered through a 0.45 µm filter and added to 30% to 80% confluent cells. After incubation, the cells were trypsinized, washed with FACS buffer and analyzed for GFP expression by FACS. In the experiments where MCF7 and SKBR3 were co-cultured, ErbB2 expression was quantitated by FACS using the anti-ErbB2 mouse mAb 4D5 which binds ErbB2 ECD (10 µg/ml) (1 hr), biotinylated sheep anti-mouse immunoglobulins (Amersham) and streptavidin-Phycoerythrin.

C) Results

1) Internalization of ErbB2 Binding Monovalent and Multivalent F5 Phage Particles by ErbB2 Expressing Cells We isolated the anti-ErbB2 scFv-F5 from a library of scFv displayed on the surface of bacteriophage as fusions to pIII (Sheets et al. (1998) *Proc. Natl. Acad. Sci. USA* 95(11): 6157–6162) by selection on ErbB2 expressing SKBR3 breast tumor cells and recovery of infectious phage from within the cell (M. Poul et al., manuscript in preparation). This selection strategy was employed to select scFv capable of undergoing endocytosis upon receptor binding. When the pHEN-F5 phagemid vector is rescued with VCS-M13 helper phage, the resulting virus particles (F5-phagemid) display an average of 1 copy of scFv-pIII fusion protein and 3 to 4 copies of the wild type pIII minor coat protein from the helper phage (Marks et al. (1992) *J. Biol Chem.* 267(23): 16007–16010). As a result, the phagemid bind monovalently. To improve the binding of the virus particles to ErbB2 expressing cells, multivalent phage antibodies were created by subcloning the F5 scFv DNA into the phage vector fd-Sfi/Not for fusion with the pII protein. Virus particles, referred to as fd-F5 phage, display 4 to 5 copies of scFv-pIII fusion protein (Id.).

To determine whether F5 phage antibodies could be internalized by mammalian cells, SKBR3 cells overexpressing ErbB2 were incubated for 16 hrs with fd-F5 phage ($10^9$ colony forming unit/ml, cfu/ml), F5 phagemid ($10^{11}$ cfu/ml), or with phagemids displaying an irrelevant anti-botulinum scFv-pIII fusion protein ($10^{12}$ cfu/ml) (Amersdorfer et al., 1997) as a negative control. The cell surface was stripped of phage antibodies using low pH glycine buffer, the cells permeabilized and fixed, and intracellular phage detected with anti-M13 antibody. Remarkably, all cells showed strong intracellular staining when incubated with fd-F5 phage or with F5 phagemid but not when incubated with the anti-botulinum phagemid. This demonstrates the dependence of phage entry on the specificity of the scFv fused to pIII.

2) Preparation of ErbB2 Binding Phages and Phagemids Packaging a Reporter Gene for Expression in Eukaryotic Cells Two strategies were used to investigate whether F5 phage could deliver a reporter gene to mammalian cells leading to expression. To make monovalent phage containing a reporter gene, we cloned the gene for green fluorescent protein (GFP) driven by the CMV promoter into the phagemid vector pHEN-F5 generating the vector pHEN-F5-GFP (FIG. 6, left panel). *Escherichia. coli TG*1 containing pHEN-F5-GFP (ampicillin resistant) were infected with helper phage (kanamycin resistant) and high titers of monovalent F5-GFP phagemids were obtained ($5.0 \times 10^{10}$ ampicillin resistant cfu/ml of culture supernatant). The ratio of packaged phagemid DNA versus helper phage DNA (ampicillin versus kanamycin resistant cfa) was determined to be 100:1. To make multivalent phage containing a reporter gene, fd-F5-GFP phage were generated by infecting *E. coli* TG1 carrying the pcDNA3-GFP phagemid (ampicillin resistant) with fd-F5 phage (tetracycline resistant), thus using fd-F5 phage as a helper phage. The fd-F5-GFP phage titer was approximately $5.0 \times 10^8$ ampicillin resistant cfu/ml of culture supernatant. Lower phage titers result when fd is used as a helper phage because it lacks a plasmid origin of replication leading to interference from the phagemid f1 origin (Cleary and Ray (1980) *Proc. Natl. Acad. Sci. USA* 77(8): 4638–4642). The ratio of packaged reporter gene DNA versus phage DNA (ampicillin versus tetracycline resistant cfu) was 1:1. The lower ratio of reporter gene/helper genome when using fd as a helper phage is due to the presence of a fully functional packaging signal on the fd genome compared to the mutated packaging signal in VCS-M13 (Vieira and Messing (1987) *Meth. Enzymol.* 153: 3–11). Both phage and phagemid preparations were assessed for SKBR3 cell binding (FIG. 7). While both preparations bound SKBR3 cells, binding could be detected with as little as $10^8$ cfu/ml of fd-F5-GFP phage cfu/ml (160 femtomolar) compared to $10^{10}$ cfu/ml of F5-GFP phagemids (15 picomolar). Thus multivalent binding leads to an increase in the apparent binding constant of virus particles.

3) Targeted Phagemid and Phage Mediated Gene Transfer into ErbB2 Expressing Breast Cancer Cells To determine if ErbB2 binding phagemids were capable of targeted gene delivery, $2.0 \times 10^5$ SKBR3 cells (a breast tumor cell line expressing high levels of ErbB2) or $2.0 \times 10^5$ MCF7 cells (a low ErbB2 expressing breast tumor cell line) were incubated with $5.0 \times 10^{11}$ cfu/ml F5-GFP phagemids at 37° C. Cells were analyzed for GFP expression by FACS after 48 hrs (FIG. 8A). 1.37% of the SKBR3 cells expressed GFP after incubation with F5-GFP phagemids (FIG. 8A6). GFP expression was identical regardless of the orientation of the f1 packaging signal (data not shown), indicating that transcription/translation was proceeding via synthesis of the complementary DNA strand. GFP expression was not detected in SKBR3 cells incubated with no phage or with helper phage packaging the reporter gene (FIG. 8A4 and 8A5). Expression was also not seen in MCF7 cells incubated with no phage, helper phage or pHEN-F5-GFP, indicating the requirement of ErbB2 expression for targeted gene delivery (FIG. 8A1, 8A2 and 4A3). Since gene transfer applications are likely to involve targeting of specific cells in an heterogeneous cell population, we performed the same experiment on a co-culture of SKBR3 and MCF7 cells (FIG. 8B). Cells were stained for ErbB2 expression to discriminate MCF7 from SKBR3 cells and the GFP expression of each subpopulation was analyzed by FACS. Only SKBR3 cells (1.91%) expressed GFP. Similar results were found using F5-GFP phages instead of F5-GFP phagemids (data not shown). These data confirm that fd-F5-GFP phage and F5-GFP phagemid mediated gene delivery is restricted to ErbB2 overexpressing cells and can be targeted to such cells in the presence of non-expressing cells.

4) Characterization of Phage Mediated Gene Transfer

To determine the dose-response characteristics of phage mediated gene transfer, SKBR3 cells were incubated for 60 hrs with increasing amounts of fd-F5-GFP phage or F5-GFP phagemids and the percent of GFP positive cells determined (FIGS. 9A and 9B). The minimal phage concentration required for detection of a significant number of GFP positive cells (FIG. 9A) was approximately $4.0 \times 10^7$ cfu/ml for fd-F5-GFP phage (0.13%) and $1.0 \times 10^{10}$ cfu/ml for F5-GFP phagemid (0.12%). The values correlate closely with the binding curves (FIG. 7) and indicate that multivalent phage are 100 to 1000 time more efficient than phagemids in terms of gene expression. No significant number of positive cells were observed with up to $4.0 \times 10^{13}$ cfu/ml of helper phage packaging the reporter gene. For both phage and phagemid, the percent of GFP positive cells increased with phage concentration with no evidence of a plateau. The maximum values achieved were 2% of cells for fd-F5-GFP phage and 4% for F5-GFP phagemids and appear to be limited by the phage titer applied ($1.5 \times 10^9$ cfu/ml and $4.0 \times 10^{12}$ cfu/ml respectively). The amount of GFP expressed per cell (estimated by the mean fluorescent intensity (MFI), FIG. 9B) also increased with phage concentration, with a small number of cells showing expression with phage titers as low as $2.0 \times 10^7$ cfu/ml (fd-F5-GFP phage) to $1.0 \times 10^{10}$ cfu/ml (F5-GFP phagemid).

To compare the yield of gene expression obtained with phage to traditional transfection methods, single stranded (ssDNA) or double stranded (dsDNA) was transfected into SKBR3 using lipofectamine. Per µg of ss DNA, efficiency of phagemid mediated gene delivery (approximately 1%) was comparable to lipofectamine transfection of ssDNA (0.98%) and dsDNA (1.27%) (Table 8). Efficiency was approximately 500 fold higher for phage mediated transfection, with 2.25 ng of ss DNA resulting in transfection of 0.87% of cells.

TABLE 8

Transfection efficiencies in SKBR3 cells.

| Transfection method | Reporter plasmid | | Amount of reporter plasmid DNA | % of GFP positive cells* |
|---|---|---|---|---|
| F5-phagemid Mediated | pHEN-F5-GFP | | 15 µg | 3.84 |
|  |  |  | 3.1 µg | 1.44 |
|  |  |  | 0.78 µg | 0.64 |
| fd-F5-phage mediated | pcDNA3-GFP | | 5 ng | 1.69 |
|  |  |  | 2.25 ng | 0.87 |
|  |  |  | 1.25 ng | 0.57 |
| Helper phage mediated | pN$_2$GFP | | 100 µg | 0.12 |
|  |  |  | 20 µg | 0.07 |
|  |  |  | 5 µg | 0.06 |
| Lipofectamine | pN$_2$GFP | dsDNA | 1 µg | 1.27 |
|  |  | ssDNA | 1 µg | 0.98 |

*Cells were analysed 48 hours after transfection for GFP expression using FACS. Results are expressed in % of GFP positive cells.
**For phage, the amount of reporter plasmid was calculated from the plasmid size and the number of ampicillin (pHEN-F5-GEP or pcDNA3-GFP) or kanamycin (pN2GFP) resistant colonies. Mock transfected cells contained an average of 0.05% GFP positive cells.

To determine the time course of gene expression, $5.0 \times 10^{11}$ cfu/ml of F5-GFP phagemid were incubated with SKBR3 cells. After 48 hrs, the culture medium was replaced by fresh medium. GFP expressing cells can be detected within 24 hrs after phage are applied and the percentage of positive cells increases linearly with increasing time to a maximum of 4.5% by 120 hours (FIG. 9C). The GFP content of the positive cells, as estimated by the MFI, increases up to 96 hrs (FIG. 9D). After 96 hrs, the number of GFP positive cells continues to increase but the MFI decreases, probably due to the repartition of GFP molecules to daughter cells during cell division.

C) Discussion

We demonstrate that filamentous phage displaying an anti-ErbB2 scFv antibody fragment as a genetic fusion with the minor coat protein pIII can be directly targeted to mammalian cells expressing the specificity of the scFv. Such phage undergo receptor mediated endocytosis and enter an intracellular trafficking pathway which ultimately leads to reporter gene expression. This is a remarkable finding demonstrating that prokaryotic viruses can be re-engineered to infect eukaryotic cells resulting in expression of a portion of the bacteriophage genome. Gene expression was detected with as few as $2.0 \times 10^7$ cfu of phage and increased with increasing phage titer up to 4% of cells. Multivalent display decreased the threshold for detectable gene expression approximately 500 fold compared to monovalent display, most likely due to an increase in the functional affinity and an increased rate of receptor mediated endocytosis from receptor crosslinking. The maximum percent of cells transfected, however, was higher for monovalent display (phagemid) due to the significantly higher phage titer generated. The lower titer of multivalent phage is due to interference of the f1 origin of replication on the reporter phagemid with the fd phage antibody origin of replication (Cleary and Ray (1980) Proc. Natl. Acad. Sci. USA 77(8): 4638–4642).

Targeted infection of mammalian cells using phage which bind endocytosable receptors is likely to be a general phenomenon. For example, fusing an anti-transferrin receptor scFv to gene III of pHEN-GFP results in GFP expression in 10% of MCF7 cells, 4% of SKBR3 cells, 1% of LNCAP cells and 1% of primary melanoma cells. Similarly, targeted GFP gene delivery to FGF receptor expressing cells using biotinylated phage and a streptavidin-FGF fusion molecule was recently reported (Larocca et al. (1998) Hum. Gene Ther. 9: 2393–2399). However, direct genetic fusion of the targeting molecule via gene III may be more efficient than using adapter molecules. Thus while the maximum percent of cells transfected using the FGF-adapter molecule was not reported, we estimate it to be only 0.03% of FGF expressing L6 rat myoblasts based on the number of cells infected, the time after infection to the measurement of gene expression and the number of cells expressing GFP. While a greater frequency of expression (0.5%) was seen in COS-1 cells, this results from the presence of large T antigen and SV40 mediated DNA replication and thus is not generalizable to most cells.

The approach we describe represents a novel method to discover ligands for targeted intracellular drug or gene delivery. Phage antibody or peptide libraries are first selected for endocytosis by mammalian cells (Barry et al. (1996) Nat. Med. 2: 299–305) or for binding to purified antigen, cells, tissues or organs. After subcloning the selected scFv genes into the pHEN-GFP vector, phage produced from individual colonies can be directly screened for gene expression. This is possible since expression can be detected with as little as $1.0 \times 10^{10}$ cfu of phagemids. This permits not only direct identification of endocytosed scFv but also the subset of receptor antibodies which undergo proper trafficking for gene expression. If multivalent display is necessary for efficient endocytosis, the scFv genes can be subcloned into fd-Sfi-Not which is then used to rescue the reporter phagemid. Use of scFv-fd phage also allows the targeting of a large number of different reporter genes in various expression vectors since many commercially available mammalian vectors contain f1 origins of replication. As such, antibody targeted phage might prove useful transfection reagents, especially for cells difficult to transfect by standard techniques.

It may also prove possible to use this approach to directly select, rather than screen, antibodies for targeted gene delivery. For example, mammalian cells are incubated with a phage antibody library containing the GFP gene, and then sorted based on GFP expression using FACS. Phage antibody DNA would be recovered from the mammalian cytoplasm by cell lysis and used to transfect E. coli and prepare more phage for another round of selection. If the quantities of recoverable phage DNA are inadequate, inclusion of the neomycin gene in the pHEN-GFP vector would permit selection of GFP expressing mammalian cells using G418 (Larocca et al. supra).

Finally, this system has promise as a targetable in vitro or in vivo gene therapy vehicle. The main limitations are infection efficiency, pharmacokinetics and immunogenicity. With respect to infection efficiency, values achieved by targeted phage in this report ($8.0 \times 10^4$/ml of phage preparation) are not dissimilar to values reported for targeted retrovirus ($10^3$–$10^5$/ml of virus) (Kasahara et al. (1994) Science 266: 1373–1376; Somia et al. (1995) Proc. Natl. Acad. Sci. USA 92(16): 7570–7574) but less than reported for adenovirus targeting strategies (Douglas et al. (1996) Nat. Biotechnol. 14: 1574–1578; Watkins et al. 1997) Gene Ther. 4(10): 1004–1012). The factors limiting higher infection efficiencies, however, are likely to differ between the systems. Thus while the percentage of cells infected by retrovirus is significantly higher than observed for bacteriophage, infection is limited by the problems encountered producing large numbers of virus which can enter the cell. Since all cells take up the targeted phage, gene expression is limited by one or several post-uptake events (e.g. degradation of phage to release DNA, endosomal escape, nuclear targeting or transcription). More detailed study of the fate of the phage and its DNA is likely to suggest where the block lies permitting engineering of phage to increase infection efficiency. For example, endosomal escape could be enhanced by co-administering replication defective adenovirus (Curiel et al. (1991) Proc. Natl. Acad. Sci. USA 88(19): 8850–8854) or incorporating endosomal escape peptides (Wagner et al. (1992) Proc. Natl. Acad. Sci. USA 89(17): 7934–7938) or proteins (Fominaya and Wels (1996) J. Biol. Chem. 271(18): 10560–10568) into the phage major coat protein pVIII. Alternatively, infection efficiency could be increased combinatorially by creating scFv targeted libraries of pVIII mutants and selecting for increased gene expression. With respect to pharmacokinetics, though not extensively studied, it is likely that the biodistribution of phage is limited to the intravascular space. This would not affect in vitro phage gene therapy, but might limit in vivo uses to those targeting the vasculature. This still leaves numerous applications including those where neovascularization plays a role, such as cancer. With respect to immunogenicity, it is likely that phage will be immunogenic, thus limiting the number of times that phage could be administered in vivo. Alternatively, it might prove possible to evolve the major coat protein pVIII to reduce or eliminate immunogenicity for example by negatively selecting a pVIII library on immune serum (Jenne et al. (1998) J. Immunol. 161(6): 3161–3168).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of selecting a polypeptide that is internalized into a target cell, said method comprising:
   i) contacting one or more target cells with one or more members of a phage display library displaying one or more polypeptides;
   ii) culturing the one or more target cells and enriching internalized library members under conditions where said internalized library members of said phage display library are enriched at least 30-fold as compared to on-internalized library members, wherein at least 30-fold enrichment is achieved in a single repetition of step I) and ii); and
   iii) identifying internalized library members of said phage display library, thereby selecting for a polypeptide that is internalized into the target cell.

2. The method of claim 1, wherein said phage display library is an antibody phage display library.

3. The method of claim 2, wherein said antibody phage display library displays single chain antibody Fv regions.

4. The method of claim 1, wherein said identifying comprises recovering internalized phage and repeating steps (i) through (iii) to further select for internalizing binding moieties.

5. The method of claim 4, wherein said recovering comprises: (a) lysing said target cells to release internalized phage; and (b) infecting a bacterial host with said internalized phage to produce phage for a subsequent round of selection.

6. The method of claim 4, wherein said recovering comprises recovering nucleic acids encoding the phage-displayed antibody.

7. The method of claim 1, wherein said identifying comprises detecting expression of a reporter gene or a selectable marker.

8. The method of claim 1, wherein said target cells form an adherent layer in said method.

9. The method of claim 1, wherein said phage express a selectable marker.

10. The method of claim 9, wherein said selectable marker is selected from the group consisting of a fluorescent protein, an antibiotic resistance gene, and a chromagenic gene.

11. The library of claim 10, wherein said chromagenic gene is selected from the group consisting of horse radish peroxidase, B-lactamase, luciferase, and B-galactosidase.

12. The method of claim 1, wherein said target cells are selected from the group consisting of solid tumor cells, members of a cDNA expression library, cells that overexpress a cytokine receptor, cells that overexpress a growth factor receptor, metastatic cells, cells of a transformed cell line, cells transformed with a gene or cDNA encoding a specific surface target receptor, and neoplastic cells derived from outside a solid tumor.

13. The method of claim 1, wherein said method further comprises contacting the members of the phage display library with cells of a subtractive cell line.

14. The method of claim 13, wherein said cells of a subtractive cell line are present in at least 2-fold excess over said target cells.

15. The method of claim 13, wherein said cells of a subtractive cell line are selected from the same tissue type as the target cells.

16. The method of claim 13, wherein said cells of a subtractive cell line are selected from the group consisting of fibroblasts, monocytes, stem cells, and lymphocytes.

17. The method of claim 13, wherein said method further comprises contacting the members of the phage display library with live cells of a subtractive cell line.

18. The method of claim 1, wherein culturing said target cells and enriching internalized library members comprises contacting the target cells with a low pH wash.

19. The method of claim 13, wherein culturing said target cells and enriching internalized library members comprises contacting the target cells with a low pH wash.

20. The method of claim 1, wherein culturing said target cells and enriching internalized library members comprises trypsinizing the target cells.

21. The method of claim 13, wherein culturing said target cells and enriching internalized library members comprises trypsinizing the target cells.

22. The method of claim 13, wherein the target cells are cells that are transformed a nucleic acid that encodes and expresses a target receptor and the subtractive cell line is the non-transformed cell line.

23. A method of selecting a polypeptide that is internalized into a target cell, comprising:
  i) contacting one or more target cells with one or more members of a phage display library displaying one or more polypeptides;
  ii) culturing the one or more target cells under conditions wherein members of said phage display library bound to an internalizing marker become internalized;
  iii) reducing non-internalized members of said phage display library by removing phage trapped in an extracellular matrix; and
  iv) identifying members of said phage display library that are internalized into one or more of said target cells, where the internalized library members of said phage display library each display polypeptide that is internalized into a target cell.

24. The method of claim 23, wherein removing the phage trapped in the extracellular matrix comprises washing the one or more target cells with a stripping buffer comprising 50 mM glycine pH 2.8, 0.5 M NaCl, 2M urea, and 2% polyvinylpyrolidone.

25. The method of claim 23, wherein removing the phage trapped in the extracellular matrix comprises trypsinizing the one or more target cells.

26. The method of claim 23, wherein said phage display library is an antibody phage display library.

27. The method of claim 23, wherein said antibody phage display library displays single chain antibody Fv regions.

28. The method of claim 23, wherein identifying the internalized library members comprises recovering internalized phage and repeating steps (i) through (iv) to further select for internalizing binding moieties.

29. The method of claim 28, wherein said recovering comprises: (a) lysing said target cells to release internalized phase; and (b) infecting a bacterial host with said internalized phage to produce phage for a subsequent round of selection.

30. The method of claim 28, wherein said recovering comprises recovering nucleic acids encoding the phage-displayed antibody.

31. The method of claim 23, wherein identifying the internalized library members comprises detecting expression of a reporter gene or a selectable marker.

32. The method of claim 23, wherein said target cells form an adherent lave in said method.

33. The method of claim 23, wherein said phage express a selectable marker.

34. The method of claim 33, wherein said selectable marker is selected from the group consisting of a fluorescent protein, an antibiotic resistance gene, and a chromagenic gene.

35. The library of claim 34, wherein said chromagenic gene is selected from the group consisting of horse radish peroxidase, B-lactamase, luciferase, and B-galactosidase.

36. The method of claim 23, wherein said target cells are selected from the group consisting of solid tumor cells, members of a cDNA expression library, cells that overexpress a cytokine receptor, cells that overexpress a growth factor receptor, metastatic cells, cells of a transformed cell line, cells transformed with a gene or cDNA encoding a specific surface target receptor, and neoplastic cells derived from outside a solid tumor.

37. The method of claim 23, wherein said method further comprises contacting the members of the phage display library with cells of a subtractive cell line.

38. The method of claim 37, wherein said cells of a subtractive cell line are selected from the same tissue type as the target cells.

39. The method of claim 37, wherein said cells of a subtractive cell line are selected from the group consisting of fibroblasts, monocytes, stem cells, and lymphocytes.

40. The method of claim 37, wherein said cells of a subtractive cell line are present in at least 2-fold excess over said target cells.

41. The method of claim 37, wherein said cells of a subtractive cell line are live cells.

42. The method of claim 37, wherein the target cells are cells that are transformed a nucleic acid that encodes and expresses a target receptor and the subtractive cell line is the non-transformed cell line.

* * * * *